(12) United States Patent
Kenan et al.

(10) Patent No.: US 7,807,624 B2
(45) Date of Patent: *Oct. 5, 2010

(54) METHODS AND COMPOSITIONS FOR PROMOTING ATTACHMENT OF CELLS OF ENDOTHELIAL CELL LINEAGE TO MEDICAL DEVICES

(75) Inventors: Daniel James Kenan, Chapel Hill, NC (US); Paul Theodore Hamilton, Cary, NC (US)

(73) Assignee: Affinergy, Inc., Durham, NC (US)

( * ) Notice: Subject to any disclaimer, the term of this patent is extended or adjusted under 35 U.S.C. 154(b) by 71 days.

This patent is subject to a terminal disclaimer.

(21) Appl. No.: 11/649,950

(22) Filed: Jan. 5, 2007

(65) Prior Publication Data

US 2007/0160644 A1 Jul. 12, 2007

Related U.S. Application Data

(60) Provisional application No. 60/758,029, filed on Jan. 11, 2006.

(51) Int. Cl.
*C07K 14/00* (2006.01)

(52) U.S. Cl. .............................. 514/2; 514/12; 530/350; 530/300

(58) Field of Classification Search ........................ None
See application file for complete search history.

(56) References Cited

U.S. PATENT DOCUMENTS

| 5,354,736 | A | 10/1994 | Bhatnagar |
| 5,356,433 | A | 10/1994 | Rowland et al. |
| 5,498,538 | A | 3/1996 | Kay et al. |
| 5,622,699 | A | 4/1997 | Ruoslahti et al. |
| 5,635,482 | A | 6/1997 | Bhatnagar |
| 5,643,712 | A | 7/1997 | Brasile |
| 5,744,515 | A | 4/1998 | Clapper |
| 5,866,363 | A | 2/1999 | Pieczenik |
| 5,929,060 | A | 7/1999 | Araneo |
| 6,033,719 | A | 3/2000 | Keogh |
| 6,071,890 | A | 6/2000 | Scheule et al. |
| 6,140,127 | A | 10/2000 | Sprague |
| 6,180,084 | B1 | 1/2001 | Ruoslahti et al. |
| 6,262,017 | B1 | 7/2001 | Dee et al. |
| 6,280,760 | B1 | 8/2001 | Meyer et al. |
| 6,306,365 | B1 | 10/2001 | Ruoslahti et al. |
| 6,436,132 | B1 | 8/2002 | Patel et al. |
| 6,559,126 | B2 | 5/2003 | Tournaire et al. |
| 6,733,755 | B2 | 5/2004 | Tchistiakova et al. |
| 6,818,620 | B2 | 11/2004 | Bhatnagar |
| 6,894,022 | B1 | 5/2005 | Hubbell et al. |
| 6,897,218 | B2 | 5/2005 | Casella et al. |
| 6,933,281 | B2 | 8/2005 | Ruoslahti et al. |
| 6,974,791 | B2 | 12/2005 | Wong et al. |
| 7,018,615 | B2 | 3/2006 | Ruoslahti et al. |
| 7,030,213 | B2 | 4/2006 | Pierschbacher et al. |
| 7,037,332 | B2 | 5/2006 | Kutryk et al. |
| 7,060,681 | B2 | 6/2006 | Hubbell et al. |
| 7,067,619 | B2 | 6/2006 | Ruoslahti et al. |
| 7,208,011 | B2 | 4/2007 | Shanley et al. |
| 7,238,669 | B2 | 7/2007 | Bishop-Hurley et al. |
| 7,390,526 | B2 | 6/2008 | Stupp et al. |
| 7,396,656 | B2 | 7/2008 | Lin et al. |
| 7,544,661 | B2 | 6/2009 | Stupp et al. |
| 7,597,924 | B2 | 10/2009 | Kondyurin et al. |
| 7,608,581 | B2 * | 10/2009 | Hamilton et al. ............... 514/2 |
| 7,625,552 | B2 | 12/2009 | Helmus et al. |
| 7,670,605 | B2 | 3/2010 | Hubbell et al. |
| 7,700,563 | B2 | 4/2010 | Pena et al. |
| 7,709,439 | B2 | 5/2010 | Helmus et al. |
| 2003/0166004 | A1 | 9/2003 | Gyuris et al. |
| 2003/0185870 | A1 | 10/2003 | Grinstaff et al. |
| 2003/0203038 | A1 | 10/2003 | Vail |
| 2003/0229393 | A1 | 12/2003 | Kutryk et al. |
| 2004/0127640 | A1 | 7/2004 | Belcher et al. |
| 2004/0258726 | A1 | 12/2004 | Stupp et al. |
| 2005/0085623 | A1 | 4/2005 | Balian |

(Continued)

FOREIGN PATENT DOCUMENTS

| WO | WO2008008266 A2 | 1/2008 |
| WO | WO2009026158 A2 | 2/2009 |

OTHER PUBLICATIONS

Binetruy-Tournaire et al., "Identification of a peptide blocking VEGF-meidated angiogenesis"; EMBO Journal, vol. 19, No. 7, pp. 1525-1533, 2000.

Giordano et al., "Biopanning and rapid analysis of selective interactive ligands"; Nature Medicine, vol. 7, No. 11, pp. 12491253, 2001.

Hetian et al., "A novel peptide isolated from a phage display library inhibits tumor growth and metastasis by blocking the binding of VEGF to its kinase domain receptor"; Journal of Biological Chemistry, vol. 277, No. 45, pp. 43137-43142, 2002.

El-Mousawi et al., "A VEGF high affinity receptor 1-specific peptide with antiangiogenic activity identified using a phage display library"; Journal of Biological Chemistry, vol. 278, No. 21, pp. 46681-46691, 2003.

Zhi et al. "Characterization of a specific phage-displayed peptide binding to vasculature of human gastric cancer"; Cancer Biology & Therapy, vol. 3, No. 12, pp. 1232-1235, 2004.

(Continued)

*Primary Examiner*—Hope A Robinson
(74) *Attorney, Agent, or Firm*—Laura L. Kiefer

(57) ABSTRACT

The present invention provides compositions and methods for an improved coating for medical devices. Provided is a biofunctional coating composition comprising at least one binding domain that has binding specificity for a surface material of a medical device, and at least one binding domain that has binding specificity for cells of endothelial cell lineage. Methods for coating a surface of a medical device, and for manufacturing of a medical device, comprise contacting the surface to be coated with the biofunctional coating material in an amount effective to form a coating, and may further comprise contacting the coated surface with cells of endothelial cell lineage to bind the cells of endothelial cell lineage to the coated surface.

22 Claims, No Drawings

U.S. PATENT DOCUMENTS

| | | | |
|---|---|---|---|
| 2005/0187162 | A1 | 8/2005 | Dhanaraj |
| 2005/0271701 | A1 | 12/2005 | Cottone, Jr. et al. |
| 2006/0121012 | A1 | 6/2006 | Kutryk et al. |
| 2006/0123505 | A1 | 6/2006 | Kikuchi et al. |
| 2006/0135476 | A1 | 6/2006 | Kutryk et al. |
| 2006/0153775 | A1 | 7/2006 | Von Wronski et al. |
| 2006/0160743 | A1 | 7/2006 | Zhang et al. |
| 2006/0223756 | A1 | 10/2006 | Liau et al. |
| 2007/0050007 | A1 | 3/2007 | Kondyurin et al. |
| 2007/0104758 | A1 | 5/2007 | Hamilton et al. |
| 2007/0160644 | A1 | 7/2007 | Kenan et al. |
| 2007/0264227 | A1 | 11/2007 | Lutolf et al. |
| 2008/0131425 | A1 | 6/2008 | Garcia et al. |
| 2009/0319020 | A1 | 12/2009 | Kassab |
| 2010/0023111 | A1 | 1/2010 | Kondyurin et al. |

OTHER PUBLICATIONS

D'Andrea et al., "Targeting angiogenesis: structural characterization and biological properties of a de novo engineered VEGF mimicking peptide"; PNAS, vol. 102, No. 40, pp. 14215-14220, 2005.

Guo et al., "Identification of peptides inhibiting adhesion of monocytes to the injured vascular endothelial cells through phage-displaying screening"; Acta Biochim Biophys Sina (Shanghai), vol. 37, No. 4, pp. 227-233, 2005. *Note: only Abstract was available.*

Whaley et al., "Selection of peptides with semiconductor binding specificity for directed nanocrystal assembly"; Nature, 405: 665-668, 2000.

Gilbert et al., "Chimeric peptides of statherin and osteopontin that bind hydroxyapatite and mediate cell adhesion"; The Journal of Biological Chemistry, 275(21): 16213-16218, 2000.

Written Opinion of the International Searching Authority for PCT/US08/61200, Sep. 29, 2008.

Liang et al., "Screening and identification of vascular-endothelial-cell-specific binding peptide in gastric cancer"; Journal of Molecular Medicine, 84: 764-773, 2006.

Harris et al., "*Staphylococcus aureus* adhesion to titanium oxide surfaces coated with non-functionalized and peptide-functionalized poly(l-lysine)-grafted-poly(ethylene glycol) copolymers"; Biomaterials, 25: 4135-4118, 2004.

Griese et al., "Isolation and transplantation of autologous circulating endothelial cells into denuded vessels and prosthetic grafts: implications for cell-based vascular therapy"; Circulation, 108: 2710-2715, 2003.

Werner et al., "Intravenous transfusion of endothelial progenitor cells reduces neointima formation after vascular injury"; Circulation Research, 93: e17-24, 2003.

Walter et al., "Statin therapy accelerates reendothelialization: a novel effect involving mobilization and incorporation of bone marrow-derived endothelial progenitor cells"; Circulation, 105: 3017-3024, 2002.

Kaushal et al., "Functional small-diameter neovessels created using endothelial progenitor cells expanded ex vivo"; Nature Medicine, 7(9): 1035-1040, 2001.

Lefkowitz and Willerson, "Prospects for cardiovascular research"; JAMA, 285: 581-587, 2001.

Bhattacharya et al., "Enhanced endothelialization and mirovessel formation in polyester grafts seeded with CD34(+) bone marrow cells"; Blood, 95: 581-585, 2000.

Topol and Seruys, "Frontiers in interventional cardiology"; Circulation, 98: 1802-1820, 1998.

Written Opinion for the International Searching Authority for PCT/US08/80321, Mar. 17, 2009.

* cited by examiner

METHODS AND COMPOSITIONS FOR PROMOTING ATTACHMENT OF CELLS OF ENDOTHELIAL CELL LINEAGE TO MEDICAL DEVICES

CROSS REFERENCE TO RELATED APPLICATIONS

This is a nonprovisional application which claims priority benefit of U.S. Provisional Application No. 60/758,029, filed 11 Jan. 2006; which is hereby incorporated by reference herein.

FIELD OF THE INVENTION

The present invention relates to methods for promoting the attachment of cells of endothelial cell lineage to an intravascular device.

BACKGROUND OF THE INVENTION

Atherosclerosis causes stenosis and occlusion of arteries. Stenting and bypass surgery are often used to treat severe disease in small caliber arteries (defined as less than 6 mm in diameter). Arterial bypass procedures are limited by the availability of a vascular conduit, such as internal mammary artery or saphenous vein. Unfortunately, synthetic conduits made from polytetrafluoroethylene (PTFE) or polyethylene terephthalate (PET) suffer from unacceptably high rates of thrombosis in small caliber grafts due to their lack of an adherent, quiescent endothelium. Hence, developing a non-thrombogenic, small caliber arterial replacement has emerged as one of the most important goals of cardiovascular intervention in the elderly population.

Intravascular devices are placed within body vasculature; typically, at a site of occlusion in a vessel or the heart, or to replace or support a vessel or portion of the heart. Intravascular devices are normally manufactured from biologically inert materials intended to reduce the complications of insertion of a foreign object into the vasculature, such as stainless steel, titanium, polymers, or a combination thereof. However numerous problems have been reported to be associated with these devices, including thrombosis, neointima formation, and restenosis. Attempts have been made to reduce or eliminate the complications of intravascular devices. For example, to address the problem of thrombosis, an individual with an intravascular device may receive an anticoagulant and anti-platelet drugs, such as ticlopidin or aspirin.

One approach to overcome complications associated with intravascular devices is a strategy to promote rapid endothelialization of the surface of the device in contact with vasculature and/or blood. In that regard, U.S. Pat. No. 7,037,332 describes a medical device having a matrix coating made by cross-linking to the matrix an antibody having binding specificity for an endothelial cell antigen, for promoting attachment of endothelial cells to the medical device. U.S. Pat. No. 6,897,218 discloses metal complexes of a piperazine derivative, which are described as promoting re-endothelialization, but which do not appear to directly bind to a device, and appear to rely on large volumes of a blood-circulating composition to be effective. U.S. Pat. No. 6,140,127 describes a method of coating a stent by applying a polymer layer, applying pyridine and tresyl chloride, and applying a five amino acid peptide (glycine-arginine-glutamic acid-aspartic acid-valine; SEQ ID NO:157) for adhering cells to the stent. U.S. Pat. No. 5,929,060 discloses derivatives of the steroid DHEA, which are described as useful for re-endothelialization. U.S. Pat. No. 5,643,712 discloses coating of vessels of an organ or tissue to be grafted with a partially polymerized extracellular matrix preparation derived from endothelial cells, which may serve as a surface promoting re-endothelialization. Device design may be modified to promote the occurrence of re-endothelialization. U.S. Pat. No. 6,436,132 discloses an intraluminal prosthesis for treating a stenotic region in a blood vessel. The openings in the stent are said to allow for re-endothelialization of the blood vessel.

Cells of the endothelial cell lineage include endothelial cells and endothelial progenitor cells. Endothelial cells line all parts of the vasculature, where they regulate coagulation, inflammation, vascular permeability, and nutrient exchange between the blood and the interstitium. In areas where the endothelium is focally denuded, coagulation rapidly ensues. Focal coagulation of a blood vessel can lead to thrombosis and vascular occlusion, or other thromboembolic events. Endothelial progenitor cells have been shown to contribute to angiogenesis and vasculogenesis in a variety of model systems, and also to contribute to endothelialization of endovascular grafts in animal models. However, spontaneous endothelialization of endovascular grafts is rare in human patients, perhaps because the graft materials are engineered to resist molecular adhesion and coagulation, and endothelial progenitor cells have no ability to adhere, survive, and proliferate on such materials. Thus, there still remains a need for methods to promote endothelialization of intravascular devices such as by treating the devices so as to promote colonization and/or growth of nascent endothelium on the treated devices.

At least two types of endothelial progenitor cells can be isolated from peripheral blood: "early" endothelial progenitor cells, which live for 2 to 4 weeks in vitro and secrete potent angiogenic factors; and "late" endothelial progenitor cells, which grow out at 3 weeks and can replicate for up to 100 population doublings. Early endothelial progenitor cells are derived from bone marrow angioblasts under the influence of vascular endothelial growth factor (VEGF). Early endothelial progenitor cells have the phenotype CD133+/−, CD34+, VEGFR-2+, CD31+, vWF-, VE-cadherin-, E-selectin-, eNOS-, and telomerase+. Late endothelial progenitor cells have the phenotype CD133+/−, CD34+, VEGFR-2+, CD31+, vWF+, VE-cadherin+, E-selectin+, eNOS+, and telomerase+. Differentiated endothelial progenitor cells are similar to late endothelial progenitor cells, except that the former are CD133(−) and telomerase(−). Other endothelial progenitor cell subpopulations, and their phenotypic markers, are being described in the art.

Desired is an approach that can do one or more of attach, recruit, support, and differentiate a nascent layer of cells of endothelial cell lineage on an intravascular device surface. For example, it is desired to have an intravascular device with a coating capable of capturing circulating cells of an endothelial cell lineage so that they are seeded on the surface of an intravascular device, with the intended benefit of reducing the occurrence of complications associated with that type of intravascular device, such as one or more of thrombosis, neointima formation, and restenosis.

SUMMARY OF THE INVENTION

The present invention provides methods for coating a surface of a medical device so as to render the coated surface capable of adhering to cells of endothelial cell lineage (e.g., one or more of endothelial cells, and endothelial progenitor cells) when the coated surface is contacted by cells of endothelial cell lineage. The present invention also provides methods for promoting adherence of cells of endothelial cell lineage to at least one surface of a medical device. The present invention also provides methods for promoting endothelialization of at least one surface of a medical device by coating at least one surface to promote attachment of cells of the endothelial cell lineage. These methods comprise contacting the at least one surface of the medical device to be coated with a biofunctional coating composition (also known as an "interfacial biomaterial") comprising at least one binding domain that specifically binds to a surface of a medical device (for ease of reference, this binding domain is referred to herein as: "surface-binding domain") which is coupled to at least one binding domain that specifically binds to cells of endothelial cell lineage (for ease of reference, this binding domain is referred to herein as: "endothelial-binding domain"). The surface-binding domain and the endothelial cell-binding domain may be coupled together directly (e.g., during synthesis, or by chemical means) or may be coupled via a linker, to form a single molecule of the biofunctional coating composition of the present invention. The biofunctional coating composition is contacted with and applied to at least one surface of a medical device in forming a coating on the medical device, and wherein the at least one endothelial-binding domain is in an amount effective in the coating for adhering cells of endothelial cell lineage to, and preferably for promoting endothelialization of, the at least one coated surface of the medical device. The methods may further comprise the step of contacting the coated device with cells of endothelial cell lineage in promoting one or more of attachment, adherence, support for growth, and support for differentiation. This latter step may occur in vitro (e.g., attaching the endothelial cells prior to implantation of the device); or may occur in vivo (e.g., once implanted, the individual's endothelial cells migrate from adjacent arterial areas of intact endothelium, or are present as circulating cells, to come in contact with, and adhere to, the surface of the device coated by the biofunctional coating composition).

Also provided are compositions according to the present invention including: a biofunctional coating composition comprising at least one surface-binding domain coupled to at least one endothelial-binding domain; and preferred endothelial-binding domains, and nucleic acid molecules (including vectors) encoding the preferred endothelial-binding domains. With respect to the methods and compositions according to the present invention, at least one surface-binding domain may comprise a single type (e.g., that binds specifically to one or more metals, for example, stainless steel), or may comprise multiple types (e.g., one type that binds specifically to one material, for example, stainless steel; and another type that binds specifically to a polymer, for example, polylactic acid). Similarly, at least one endothelial-binding domain may comprise a single type (e.g., that binds specifically to a subset of cells of endothelial cell lineage; for example, to endothelial cells only; or with broad specificity (e.g., in general, for both endothelial cells and endothelial progenitor cells)), or may comprise multiple types (e.g., one type that binds specifically to endothelial cells; and another type that binds specifically to endothelial progenitor cells). In a preferred embodiment, the biofunctional coating composition used in the method according to the present invention comprises an endothelial binding domain comprising peptide having an amino acid sequence illustrated in one or more of SEQ ID NO:95, SEQ ID NO:96, SEQ ID NO:97, and SEQ ID 98.

In another embodiment, the invention relates to a method of promoting the adherence of cells of endothelial cell lineage to a medical device, and more preferably an intravascular device. Also provided is a method for manufacturing a medical device. These methods comprise contacting at least one surface of a medical device with a biofunctional coating composition (which binds specifically to cells of endothelial cell lineage) in forming at least one coated surface; and contacting the at least one coated surface with cells of endothelial cell lineage (e.g., in promoting adherence of cells of endothelial cell lineage to the at least one coated surface); wherein the biofunctional coating composition comprises at least one surface-binding domain and at least one endothelial-cell binding domain; and wherein the at least one surface-binding domain and the at least one endothelial-cell binding domain are coupled together. Contacting of cells of endothelial cell lineage with the biofunctional coating composition on the medical device can be by any method known in the art for promoting binding interactions between an affinity molecule and its ligand, such as, for example, incubating, dipping, spraying, or brushing a solution containing cells of endothelial cell lineage onto the medical device comprising the biofunctional coating composition. Also provided is a medical device comprising a coating formed by applying an effective amount of the biofunctional coating composition to a surface of the medical device, in rendering the medical device compatible for attachment of endothelial cells, and more preferably for the attachment of endothelial cells with subsequent endothelialization of the coated surface.

Alternatively, provided is a method for promoting endothelialization of a vascular device so that to a selected surface of the device, once that surface is coated and the device implanted, promoted is attachment of cells of endothelial cell lineage. The method comprises the steps of: (a) contacting a biofunctional coating composition to at least one surface of a vascular device to be endothelialized, so that the biofunctional coating composition binds to the at least one surface, in forming a coated surface on the vascular device; wherein the biofunctional coating composition comprises at least one surface-binding domain coupled to at least one endothelial-cell binding domain; and (b) implanting the device into an individual (human or non-human) in need of the device; wherein cells of endothelial cell lineage (produced by the individual) contact, attach and adhere to the coated surface of the device (primarily mediated by the cells binding to the at least one endothelial binding domain of the biofunctional coating composition), in promoting spread of cells of endothelial cell lineage over the coated surface of the device, and in promoting endothelialization of the vascular device. Promoting endothelialization on the implanted device may further promote one or more of healing of tissue or vasculature adjacent to the implanted device, promote incorporation (integration) of the implanted device into the adjacent tissue, and reduce occurrence of thrombosis as related to the implanted device.

DETAILED DESCRIPTION OF THE INVENTION

The present invention provides compositions for an improved coating for medical devices, methods of coating medical devices using those compositions, and a surface of a medical device which is coated with a biofunctional coating composition of the present invention.

Definition Section While the following terms are believed to be well understood by one of ordinary skill in the art, the following definitions are set forth to facilitate explanation of the invention.

The term "effective amount" is used herein, in referring to the biofunctional coating composition according to the present invention and for purposes of the specification and claims, to mean an amount sufficient of the biofunctional coating composition is applied to the at least one surface to be coated (via contact of the at least one surface to the biofunctional coating) so as to (a) mediate binding of the biofunctional coating composition to the at least one surface of the medical device in forming a coating; and (b) promote adherence of endothelial cells to, and more preferably, endothelialization of, the coated surface.

The term "cells of endothelial cell lineage" is used herein for purposes of the specification and claims, to mean endothelial cells at any development stage (e.g., ranging from early stages of development, such as an endothelial stem cell or progenitor cell, to a mature stage of development such as a fully differentiated, tissue specific endothelial cell); and including stem cells capable of differentiating into endothelial progenitor cells and/or endothelial cells, such stem cells sharing at least one surface molecule or receptor in common with endothelial cells (e.g., bone marrow angioblast; a cardiac Sca-1+ stem cell (which can be differentiated into endothelial cells in the presence of leukemia inhibitory factor (LIF)); an adipose-derived stem cell); or a combination thereof. Thus, cells of endothelial cell lineage include endothelial cells, endothelial progenitor cells, and stem cells capable of differentiating into endothelial cells and/or endothelial progenitor cells. A preferred cell of endothelial cell lineage may be used in accordance with the present invention to the exclusion of a cell of endothelial cell lineage other than the preferred cell of endothelial cell lineage.

The term "endothelialization" is used herein unless otherwise specified, for purposes of the specification and claims, to mean one or more of the growth (desirably including proliferation) of endothelial cells, and differentiation of endothelial cells, on and over the at least one surface of a medical device coated by an effective amount of the biofunctional coating composition according to the present invention. Preferably, once the cells of endothelial cell lineage are attached to the surface of a medical device coated by an effective amount of the biofunctional coating composition, promoted will be endothelial cell growth and development to provide an endothelial tissue layer. Thus, the term "endothelialization" can mean re-endothelialization of a vascular graft which has lost or been stripped of its endothelium due to any biological or mechanical process; or it may comprise growing new endothelial cells to cover a surface of an implanted or implantable graft, or implanted or implantable medical device, which had not been previously covered by endothelial cells.

The term "medical device" is used herein, for purposes of the specification and claims, to refer to an intravascular device, vascular device, vascular graft, a lead or lead tip exposed to the vascular system (e.g., from a cardiac pacemaker or cardiac defribillator). In a preferred embodiment, within the scope and meaning of "medical device" herein is a device comprising a stent (as known in the art, a stent being a metallic and/or polymeric cage-like or tubular support device that is used to hold vessels (e.g., blood vessels) open). The terms "intravascular device" and "vascular device" are used interchangeably herein, for purpose of the specification and claims, to refer to a structure that is introduced into a human or animal vasculature to restore function of damaged, diseased, or blocked tissue, and includes prosthetic devices, and vascular grafts. In a preferred embodiment, within the scope and meaning of "intravascular device" or "vascular device" herein is a device comprising a stent. The term "vascular device" as used herein also includes device-related materials that are associated with the device and are also introduced into a human or animal body in conjunction with the device. Representative vascular devices include, but are not limited to, heart patches, artificial heart valves, annuloplasty rings, annular rings, mechanical assist devices, vascular sealing devices, central venous catheters, arterial catheters, pacemakers, defibrillators, guidewires, embolic protection filters, embolic devices (e.g., coils), implantable infusion pumps, and vascular sutures. Vascular grafts include coronary artery bypass grafts, prosthetic heart valves, peripheral vascular bypass grafts, vascular access grafts, and synthetic grafts. A preferred medical device may be used in accordance with the present invention to the exclusion of a medical device other than the preferred medical device.

A medical device may be comprised of, and hence have one or more surfaces comprised of, a variety of materials including, but not limited to, a metal, a metal oxide, a non-metal oxide, a ceramic, a rubber, a plastic, an acrylic, a silicone, a polymer, and combinations thereof. An intravascular device can be produced using any biocompatible material; however, because of the difficulties with biocompatibilities in the vasculature, it is preferred that the biocompatible material be relatively inert. Such devices are made of a variety of materials that are known in the art, but most typically are biologically inert polymers or metals. Metals used in the manufacture of medical devices are known in the art to include, without limitation, stainless steel, tantalum, gold, platinum, silver, tungsten, titanium, titanium alloys (for example, memory titanium alloys such as nitinol), a transition metal, alkali metals, and alkaline earth metals (each of the latter three comprise metals related in structure and function, as classified in the Periodic Table). Metal alloys (e.g., cobalt-chrome alloy) and metal oxides of each of these groups, individually and separately, are included. Polymers may be used in the manufacture of a medical device and/or may be applied to a medical device as a coating of the medical device; hence, a polymer may be a surface of a medical device. Generally, hydrophilic polymers are polymers chosen for coating a medical device to form a coated surface. Polymers used for medical devices may be biodegradable (e.g., self-dissolving, bioresorbable, degradable in vivo) or non-biodegradable.

Non-limiting examples of suitable biodegradable polymers include: poly-amino acids; polyanhydrides including maleic anhydride polymers; polycarboxylic acid; polyethylene oxide; one or more of polylactic acid or polyglycolic acid (and copolymers and mixtures thereof, e.g., poly(L-lactic acid) (PLLA), poly(D,L,-lactide), poly(lactic acid-co-glycolic acid), 50/50 (DL-lactide-co-glycolide)); polyorthoesters; polydioxanone; polyphosphazenes; polypropylene fumarate; polydepsipeptides; one or more of polycaprolactone (and co-polymers and mixtures thereof, e.g., poly(D,L-lactide-co-caprolactone) or polycaprolactone co-butylacrylate; polyhydroxybutyrate valerate and blends; polycarbonates (e.g., tyrosine-derived polycarbonates and arylates), polyiminocarbonates, polydimethyltrimethylcarbonates; cyanoacrylate; calcium phosphates; polyglycosaminoglycans; macromolecules (such as polysaccharides, e.g., hyaluronic acid, cellulose, hydroxypropylmethyl cellulose); proteins and polypeptides (e.g., gelatin, collagen, albumin, and the like); and mixtures and copolymers of any of the foregoing.

Non-limiting examples of suitable non-biodegradable polymers include: inert polyaryletherketones, including polyetheretherketone ("PEEK"), polyether ketone, polyetherketoneketone, and polyetherketoneetherketoneketone; polyurethanes; polystyrene, and styrene-ethylene/butylene-styrene block copolymers; polyisobutylene copolymers and styrene-isobutylene-styrene block copolymers; polyvinylpyrrolidone; polyvinyl alcohols; copolymers of vinyl monomers; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene; copolymers of ethylene and polypropylene; polycarbonates, silicones; siloxane polymers; cellulosic polymers (e.g, cellulose acetate); polytetrafluoroethylene; polytetrafluoroethylene (e-PTFE); nylons and related polyamide copolymers; and mixtures, and copolymers (including crosslinked copolymers) of any of the foregoing.

When the term "surface" is used herein in conjunction with a medical device, generally it is referring to one or more surfaces of the medical device which is or becomes exposed to biological solutions and/or biological tissue, and preferably comes in contact with blood and/or is introduced into vasculature of an individual; and hence, such surface is susceptible to any one or more of thrombosis, neointima formation, and restenosis.

The term "individual", as used herein, for purposes of the specification and claims, refers to either a human or an animal.

The term "vascular biologic", as used herein, refers to a biological substance which has specific biologic utility in one or more of: the repair or integration of a vascular device within the vascular system, especially after surgery or upon implantation of an intravascular device; and promotion of endothelialization. A vascular biologic may comprise a biological substance selected from the group consisting of a collagen (e.g., type IV and/or type V), vitrogen, laminin, entactin, fibronectin, glycans (e.g., proteoglycans, glycosaminoglycans), one or more growth factors supporting endothelial cell growth (e.g., vascular endothelial cell growth factor (VEGF, including its variants), epidermal growth factor (EGF), fibroblast growth factor (basic fibroblast growth factor (bFGF), acidic fibroblast growth factor (aFGF)), heparin-binding epidermal-like growth factor, angiopoietin 1 (ang-1), angiopoietin 2 (ang-2), hepatocyte growth factor (HGF), platelet-derived endothelial cell growth factor (PD-ECGF), LIF), angiopoietins (e.g., ang-3, and ang-4), and a combination thereof. A preferred vascular biologic may be used in accordance with the present invention to the exclusion of a vascular biologic other than the preferred vascular biologic.

The term "surface-binding domain", used herein for purposes of the specification and claims, refers to a peptide that binds to a surface of a medical device; and more particularly, a peptide having binding specificity (including affinity) for a material comprising the surface of a medical device to be coated. In a preferred embodiment, the surface-binding domain is identified for binding specificity (with affinity) sufficient for its intended purpose (as known to those skilled in the art) by screening and/or selection methods known in the art, such as from phage display libraries. Non-limiting examples of surface-binding domains are illustrated in Tables 1 & 2, and are represented by amino acid sequences set forth in SEQ ID NOs:1-94. A preferred surface-binding domain (including the type of surface to which it binds with specificity) may be used with the present invention to the exclusion of a surface-binding domain other than the preferred surface-binding domain.

The term "time sufficient for binding" generally refers to a temporal duration sufficient for specific binding of a binding domain described herein, and a substrate for which the binding domain has binding specificity, as known to those skilled in the art.

The term "endothelial-binding domain", used herein for purposes of the specification and claims, refers to a peptide that specifically binds to one or more cells of endothelial cell lineage (as defined herein). Thus, the endothelial-cell binding domain may specifically bind to a specific type of cell of endothelial cell lineage (e.g., endothelial cells, or endothelial progenitor cell, or endothelial cells of a specific tissue origin (e.g., cardiac endothelial cells)), or to more than one type of cells of endothelial cell lineage (e.g., sharing a common surface molecule bound by the endothelial cell-binding domain). However, excluded from the definition "endothelial-binding domain" is an antibody, and more particularly an antibody having binding specificity for endothelial cells. A preferred endothelial-binding domain (including the type of cells of endothelial cell lineage to which it binds with specificity) may be used in accordance with the present invention to the exclusion of an endothelial-binding domain other than the preferred endothelial-binding domain. In a preferred embodiment according to the present invention, provided is an endothelial-binding domain comprising a peptide comprising the amino acid sequence of any one or more of SEQ ID NOs: 95, 96, 97, and 98. In another embodiment, an endothelial-binding domain, for use in a biofunctional coating or a method according to the present invention, can comprise a peptide known in the art to bind cells of endothelial cell lineage, and more specifically to endothelial cells. Non-limiting examples of peptides are also illustrated in Table 4, and may be represented by amino acid sequences set forth in SEQ ID NOs: 99-157.

The terms "biofunctional coating composition" and "interfacial biomaterial" are used interchangeably, in reference to the present invention and for purposes of the specification and claims, to refer to a composition comprising at least one surface-binding domain and at least one endothelial-binding domain, wherein the at least one surface-binding domain and at least one endothelial-binding domain are coupled together (e.g., by one or more of physically, chemically, synthetically, or biologically (e.g., via recombinant expression)) in such a way that each binding domain retains its respective function to bind to the respective molecule for which it has binding specificity. Such coupling may include a multimeric molecule having two or more surface-binding domains coupled together, wherein an endothelial-binding domain is coupled to all or only some of the surface-binding domains of the multimeric molecule. For example, using standard reagents and methods known in the art of peptide chemistry, two binding domains may be coupled via a side chain-to-side chain bond (e.g., where each of the peptides have a side chain amine (e.g., such as the epsilon amine of lysine)), a side chain-to-N terminal bond (e.g., coupling the N-terminal amine of one peptide with the side chain amine of the other peptide), a side chain-to-C-terminal bond (e.g., coupling the C-terminal chemical moiety (e.g., carboxyl) of one peptide with the side chain amine of the other peptide), an N-terminal-to-N-terminal bond, an N-terminal to C-terminal bond, a C-terminal to C-terminal bond, or a combination thereof. In synthetic or recombinant expression, a peptide of a surface-binding domain can be coupled directly to a peptide of an endothelial-binding domain by synthesizing or expressing both peptides as a single peptide. The coupling of surface-binding domain to an endothelial-binding domain may also be via a linker to form a biofunctional coating composition.

The biofunctional coating composition or interfacial biomaterial of the present invention comprises: (a) the at least one surface-binding domain in an amount effective to mediate the binding of the biofunctional coating composition or interfacial biomaterial to the surface material (e.g., metal, plastic, or polymer) of the medical device for which the at least one surface-binding domain has binding specificity; and (b) the at least one endothelial-binding domain in an amount effective to confer to the coated medical device the ability to attach or adhere to cells of endothelial cell lineage, and more preferably and additionally, to promote endothelialization of the coated surface of the medical device; wherein the at least one surface-binding domain and the at least one endothelial-binding domain are coupled together. In a preferred embodiment, a linker is used to join together the at least one surface-binding domain and the at least one endothelial-binding domain.

In function, when the biofunctional coating composition is applied to a surface of a medical device (by contacting the biofunctional coating composition with the surface), binding of the biofunctional coating composition to the surface is mediated primarily by a domain of the biofunctional coating composition comprising the surface-binding domain; and the properties of, or associated with, the biofunctional coating composition as related to attachment, adherence, endothelialization, or a combination thereof, are mediated primarily by a domain of the biofunctional coating composition comprising the endothelial-binding domain. Thus, when a medical device is coated with a biofunctional coating composition of the present invention, and then the coated medical device is introduced into or applied to an individual, the biofunctional coating composition is then the interface (hence, "interfacial biomaterial") between the medical device and the biological tissues and/or biological fluids of the individual. Accordingly, provided is a method of promoting the attachment and adherence of cells of endothelial cell lineage to a medical device, the method comprising coating one or more surfaces of the medical device with a biofunctional coating composition or interfacial biomaterial comprising at least one surface-binding domain and at least one endothelial-binding domain, wherein the at least one surface-binding domain and the at least one endothelial binding domain are coupled together. In another embodiment, provided is a method of promoting endothelialization on a surface of a medical device, the surface being suitable for contacting one or more of a biological tissue (e.g., a blood vessel) or biological fluid (e.g., blood) associated with vasculature, the method comprising coating one or more surfaces of the medical device with a biofunctional coating composition or interfacial biomaterial comprising at least one surface-binding domain and at least one endothelial-binding domain, wherein the at least one surface-binding domain and the at least one endothelial-binding domain are coupled together, and wherein the at least one endothelial-binding domain is bound to cells of endothelial cell lineage.

It is an important feature of the biofunctional coating compositions of the present invention that the biofunctional coating composition may be comprised of a single type ("type" as defined by binding specificity) of surface-binding domain (e.g., a peptide having binding specificity for a certain metal, such as titanium), or may be comprised of more than one type of surface-binding domain (i.e., different peptides, each with a different binding specificity; for example, one type of surface-binding domain which has binding specificity for a selected metal, and another type of surface-binding domain which has binding specificity for a selected polymer). Thus, each type of surface-binding domain is capable of binding to a different surface material. The surface-binding domain in the biofunctional coating composition of the present invention is selected to specifically bind (e.g., typically, noncovalently, ionically, or electrostatically) to the surface material or component of the medical device desired to be coated. In that regard, having more than one type of surface-binding domain in a biofunctional coating composition of the present invention is particularly useful for a medical device which comprises more than one type of material (or surface component) exposed to a biological tissue and/or biological fluid associated with vasculature (e.g., a surface comprised of plastic, and a surface comprised of a metal or metal oxide, or alloy; or a surface comprised of a polymer coating, and a surface comprised of a metal or metal oxide or alloy; or two or more surfaces, each comprised of a different metal or metal oxide or alloy). Similarly, the biofunctional coating compositions of the present invention may comprise a single type ("type" as defined by binding specificity) of endothelial-binding domain (e.g., a peptide having binding specificity for a certain type of endothelial cell, as defined by the surface molecules which distinguish it from other cells of endothelial cell lineage, and from other cells in general, as known in the art), or may comprise of more than one type of endothelial-binding domain (e.g., two or more different peptides, each with binding specificity for different cells of endothelial cell lineage). Thus, in such case, each type of endothelial-binding domain has a binding specificity for cells of endothelial cell lineage that differs from the binding specificity of another type of endothelial-binding domain present in the biofunctional coating composition.

The term "linker" is used, for purposes of the specification and claims, to refer to a compound or moiety that acts as a molecular bridge to couple at least two different molecules (e.g., with respect to the present invention, coupling a surface-binding domain to an endothelial-binding domain, or coupling two or more surface-binding domains in making a multimeric molecule comprised of two or more surface-binding domains, or coupling two or more endothelial-binding domains in making a multimeric molecule comprised of two or more endothelial-binding domains). Thus, for example, one portion of the linker binds to a surface-binding domain according to the present invention, and another portion of the linker binds to an endothelial-binding domain. As known to those skilled in the art, and using methods known in the art, a surface-binding domain and an endothelial-binding domain may be coupled to the linker in a step-wise manner, or may be coupled simultaneously to the linker, to form a biofunctional coating composition or interfacial biomaterial according to the present invention. There is no particular size or content limitations for the linker so long as it can fulfill its purpose as a molecular bridge, and that the binding specificities of the biofunctional coating composition are substantially retained.

Linkers are known to those skilled in the art to include, but are not limited to, chemical chains, chemical compounds (e.g., reagents), and the like. The linkers may include, but are not limited to, homobifunctional linkers and heterobifunctional linkers. Heterobifunctional linkers, well known to those skilled in the art, contain one end having a first reactive functionality (or chemical moiety) to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), amino acid linkers (typically, a short peptide of between 3 and 15 amino acids, and often containing amino acids such as glycine, and/or serine), and polymers (e.g., polyethylene glycol) may be employed as a linker with respect to the present invention. In one embodiment, representative peptide linkers comprise multiple reactive sites to be coupled to a binding domain (e.g., polylysines, polyornithines, polycysteines, polyglutamic acid and polyaspartic acid) or comprise substantially inert peptide linkers (e.g., lipolyglycine, polyserine, polyproline, polyalanine, and other oligopeptides comprising alanyl, serinyl, prolinyl, or glycinyl amino acid residues). In some embodiments wherein amino acid linker is chosen, the biofunctional coating composition may be synthesized to be a single, contiguous peptide comprising a surface-binding domain, a linker, and an endothelial-binding domain. Thus, the linker attachment is simply via the bonds of the single contiguous peptide.

Suitable polymeric linkers are known in the art, and can comprise a synthetic polymer or a natural polymer. Representative synthetic polymers include but are not limited to polyethers (e.g., poly(ethylene glycol) ("PEG")), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, polyhexanoic acid, flexible chelators such as EDTA, EGTA, and other synthetic polymers which preferably have a molecular weight of about 20 daltons to about 1,000 kilodaltons. Representative natural polymers include but are not limited to hyaluronic acid, alginate, chondroitin sulfate, fibrinogen, fibronectin, albumin, collagen, calmodulin, and other natural polymers which preferably have a molecular weight of about 200 daltons to about 20,000 kilodaltons (for constituent monomers). Polymeric linkers can comprise a diblock polymer, a multi-block copolymer, a comb polymer, a star polymer, a dendritic or branched polymer, a hybrid linear-dendritic polymer, a branched chain comprised of lysine, or a random copolymer. A linker can also comprise a mercapto(amido)carboxylic acid, an acrylamidocarboxylic acid, an acrlyamido-amidotriethylene glycolic acid, 7-aminobenzoic acid, and derivatives thereof. Linkers are known in the art and include linkers that can be cleaved, and linkers that can be made reactive toward other molecular moieties or toward themselves, for cross-linking purposes.

Depending on such factors as the molecules to be linked, and the conditions in which the linking is performed, the linker may vary in length and composition for optimizing such properties as preservation of biological function, stability, resistance to certain chemical and/or temperature parameters, and of sufficient stereo-selectivity or size. For example, the linker should not significantly interfere with the ability of a surface-binding domain to function in a biofunctional coating composition (i.e., to sufficiently bind, with appropriate avidity for the purpose, to a surface for a medical device for which it has specificity according to the present invention). Likewise, the linker should not significantly interfere with the ability of an endothelial-binding domain to function in a biofunctional coating composition (i.e., to sufficiently bind, with appropriate avidity for the purpose, to cells of endothelial cell lineage for which it has specificity according to the present invention). A preferred linker may be a molecule which may have activities which enhance or complement the effect of the biofunctional coating composition of the present invention. For example, using polyethylene glycol or other polymeric molecule or protein (e.g., albumin) as a linker may serve to help prevent non-specific protein and/or undesired cell adherence to the surface of the medical device coated with a biofunctional coating composition according to the present invention. A preferred linker may be used in the present invention to the exclusion of a linker other than the preferred linker.

The terms "binds specifically" or "binding specificity", and like terms used herein, are interchangeably used, for the purposes of the specification and claims, to refer to the ability of a binding domain (as described herein) to have a binding affinity that is greater for one target molecule or surface material selected to be bound (the latter, "target surface material") over another molecule or surface material (other than the target molecule or target surface material); e.g., an affinity for a given substrate in a heterogeneous population of other substrates which is greater than, for example, that attributable to non-specific adsorption. For example, a surface-binding domain has binding specificity for a stainless steel surface of a medical device, when the surface-binding domain demonstrates preferential binding to stainless steel, as compared to binding to another component or material of the medical device (such as a metal other than stainless steel, or a polymer). Such preferential binding may be dependent upon the presence of a particular conformation, structure, and/or charge on or within the molecule or material for which the binding domain has binding specificity, such that it recognizes and binds to that molecule or material rather than to molecules or materials in general.

In some embodiments, a binding domain that binds specifically to a particular surface, material or composition binds at least 10%, 20%, 30%, 40%, 50%, 60%, 70%, 80%, 90%, 100%, 200%, 300%, 400%, 500%, or a higher percentage, than the binding domain binds to an appropriate control such as, for example, a different material or surface, or a protein typically used for such comparisons such as bovine serum albumin. For example, binding specificity can determined by an assay in which quantitated is a signal (e.g., fluorescence, or calorimetric) representing the relative amount of binding between a peptide and target cells, as compared to peptide and non-target cells. Thus, if in such an assay, the results indicate that about 90% of the endothelial cells (as target cells) present in the assay are bound by a peptide, and less than 10% of the other cells (e.g., smooth muscle cells; "non-target cells") present in the assay are bound by the peptide, then the peptide is said to have binding specificity for endothelial cells. Such a peptide may be useful as an endothelial-binding domain in a biofunctional coating composition according to the present invention. In a preferred embodiment, the binding domain has binding specificity that is additionally characterized by an EC50 of 10 µM or less, and more preferably less than 1 µM. The EC50 can be determined using any number of methods known in the art, such as by generating a concentration response curve from a binding assay in which the concentration of the peptide is titered with a known amount of cells for which the peptide has binding specificity (see, for example, methods described in Example 1, Part B herein). In such case, the EC50 represents the concentration of peptide producing 50% of the maximal binding observed for that peptide in the assay.

The term "peptide" is used herein, for the purposes of the specification and claims to refer to an amino acid chain of no less than about 3 amino acids and no more than about 500 amino acid residues in length, wherein the amino acid chain may include naturally occurring amino acids, synthetic amino acids, genetically encoded amino acids, non-genetically encoded amino acids, and combinations thereof; however, specifically excluded from the scope and definition of "peptide" herein is an antibody. Preferably, the peptide comprising a binding domain according to the present invention comprises a contiguous sequence of no less than 7 amino acids and no more than about 60 amino acids in length. A peptide used in accordance with the present invention may be produced by chemical synthesis, recombinant expression, biochemical or enzymatic fragmentation of a larger molecule, chemical cleavage of larger molecule, a combination of the foregoing or, in general, made by any other method in the art, and preferably isolated. The term "isolated" means that the peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes. A preferred peptide may be used in the present invention to the exclusion of a peptide other than the preferred peptide.

Peptides can include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. In a preferred embodiment, and in a biofunctional coating composition according to the present invention, the at least one surface-binding domain comprises an N-terminal amino acid, a C-terminal amino acid, or a combination thereof, wherein such amino acid is a non-genetically encoded amino acid that enhances the binding avidity (strength of binding interactions) of the surface-binding domain to the surface of a medical device for which it has binding specificity. Such amino acids can be incorporated into a peptide comprising a surface-binding domain by standard methods known in the art for solid phase and/or solution phase synthesis. For example, in one embodiment, from about one to about four residues of DOPA, a hydroxy-amino acid (e.g., one or more of hydroxylysine, allo-hydroxylysine, hydroxyproline, and the like) or a combination thereof, is added as terminal amino acids of an amino acid sequence of a peptide during synthesis, wherein the peptide comprises a surface-binding domain used in the biofunctional coating composition according to the present invention for enhancing the strength of the binding interactions (e.g., via electrostatic or ionic interactions) between the biofunctional coating composition and the at least one surface of the medical device to be coated.

A peptide according to the present invention may be modified, such as by addition of chemical moieties, or substitutions, insertions, and deletions of amino acids, where such modifications provide for certain advantages in its use. Thus, the term "peptide" encompasses any of a variety of forms of peptide derivatives including, for example, amides, conjugates with proteins, cyclone peptides, polymerized peptides, conservatively substituted variants, analogs, fragments, chemically modified peptides, and peptide mimetics. Any peptide derivative that has desired binding characteristics of a binding domain according to the present invention can be used in the practice of the present invention. For example, a chemical group, added to the N-terminal amino acid of a synthetic peptide to block chemical reactivity of that amino terminus of the peptide, comprises an N-terminal group. Such N-terminal groups for protecting the amino terminus of a peptide are well known in the art, and include, but are not limited to, lower alkanoyl groups, acyl groups, sulfonyl groups, and carbamate forming groups. Preferred N-terminal groups may include acetyl, Fmoc, and Boc. A chemical group, added to the C-terminal amino acid of a synthetic peptide to block chemical reactivity of that carboxy terminus of the peptide, comprises a C-terminal group. Such C-terminal groups for protecting the carboxy terminus of a peptide are well known in the art, and include, but are not limited to, an ester or amide group. Terminal modifications of a peptide are often useful to reduce susceptibility by proteinase digestion, and to therefore prolong a half-life of peptides in the presence of biological fluids where proteases can be present. Optionally, a peptide comprising a binding domain, as described herein, can comprise one or more amino acids that have been modified to contain one or more chemical groups (e.g., reactive functionalities such as fluorine, bromine, or iodine) to facilitate linking the peptide to a linker molecule. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH).

Peptides which are useful as binding domains in a biofunctional coating composition or method of using the biofunctional coating composition according to the present invention also include peptides having one or more substitutions, additions and/or deletions of residues relative to the sequence of an exemplary peptide disclosed in any one or more of Tables 1, 2, 3, and 4 and SEQ ID NOs: 1-157 herein, so long as the binding properties of the original exemplary peptide are substantially retained. Thus, binding domain according to the present invention includes peptides that differ from the exemplary sequences disclosed herein by about 1, 2, 3, 4, 5, 6, 7, 8, 9, 10, 11, 12, 13, 14, 15, 16, 17, 18, 19, or 20 amino acids (and depending on the length of the exemplary peptide; also expressed in percent, for example, between 5% and 95% of the amino acid sequence of an exemplary peptide may be modified, as shown in Tables 1-4), but that substantially retain the ability of the corresponding exemplary sequence to bind to a particular material or to act as a binding domain with binding specificity as described herein (e.g., retains at least 25%, 50%, 75%, 100% or more of the binding specificity of an exemplary sequence disclosed herein, as measured using an appropriate assay). That is, binding domains according to the present invention preferably include peptides that share sequence identity with the exemplary sequences disclosed herein of at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity may be calculated manually or it may be calculated using a computer implementation of a mathematical algorithm, for example, GAP, BESTFIT, BLAST, FASTA, and TFASTA, or other programs or methods known in the art. Alignments using these programs can be performed using the default parameters.

For example, consider surface-binding domains comprising amino acid sequences identified in Table 1 as SEQ ID NOs: 18,19, and 21. A consensus sequence may be written (using standard single letter amino acid designations) as: FZXZXXYXBXXXL, wherein Z is either F or S, X is any amino acid, and B is H or M. Thus, these amino acid sequences share sequence identity that ranges from about 20% to about 30%, yet substantially retain binding specificity for polystyrene. In another example, surface-binding domains comprising amino acid sequences identified in Table 1 as SEQ ID NOs: 44 and 45 share sequence identity greater than 80%. In yet another example, a peptide comprising an amino acid sequence set forth in SEQ ID NO:73 was modified by substitution of the two cysteine residues within the amino acid sequence with another amino acid (e.g., serine) to result in a peptide comprising an amino acid sequence set forth in SEQ ID NO:74. Binding studies showed that the surface-binding domain comprising an amino acid sequence as set forth in SEQ ID NO:74 substantially retained binding specificity (demonstrating only a 10 fold reduction in binding) as compared to a surface-binding domain comprising an amino acid sequence set forth in SEQ ID NO:73.

A peptide having an amino acid sequence substantially identical to a sequence of an exemplary peptide disclosed herein may have one or more different amino acid residues as a result of substituting an amino acid residue in the sequence of the exemplary peptide with a functionally similar amino acid residue (a "conservative substitution"); provided that peptide containing a conservative substitution will substantially retain the binding specificity of the exemplary peptide not containing the conservative substitution. Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue such as aspartic acid or glutamic acid for another.

In yet another embodiment of the present invention, a binding domain may be described herein as comprising a peptide consisting essentially of a peptide (and/or its amino acid sequence) useful in the present invention. When used herein in reference to the present invention and for purposes of the specification and claims, the terminology "consisting essentially of" refers to a peptide which includes the amino acid sequence of the peptides described herein, and a peptide having at least 70% identity thereto (as described herein), along with additional amino acids at the carboxyl and/or amino terminal ends (e.g., ranging from about 1 to about 20 additional amino acids at one or both ends) which maintains the primary activity of the peptides as a binding domain described herein. Thus, as a non-limiting example, a peptide or "consisting essentially of" any one of the amino acid sequences illustrated as SEQ ID NOs: 95, 96, 97, and 98 will possess the activity of binding cells of endothelial cell lineage with binding specificity, as provided herein; and will not possess any characteristics which constitutes a material change to the basic and novel characteristics of the peptide as a binding domain (e.g., thus, in the foregoing example, a full length naturally occurring polypeptide, or a genetically engineered polypeptide, which has a primary activity other than as a binding domain described herein, and which contains the amino acid sequence of a binding domain comprising a peptide described in the present invention, would not constitute a peptide "consisting essentially of" a peptide described in the present invention).

[End of Formal Definition Section]

The present invention provides for a biofunctional coating composition (or interfacial biomaterial), a peptide comprising an endothelial-binding domain, methods for coating a medical device, methods for manufacturing a medical device, and a coated medical device; all relating to a biofunctional coating composition comprising at least surface-binding domain coupled to at least one endothelial-binding domain. The at least one surface-binding domain is in an amount effective to mediate the binding of the biofunctional coating composition to the selected surface of the medical device for which the at least one surface-binding domain has binding specificity; and the at least endothelial-binding domain is in an amount effective to render a surface of the medical device coated by a biofunctional coating composition according to the present invention capable of promoting one or more of attachment to, adherence of, and endothelialization with, cells of endothelial cell lineage. The present invention is illustrated in the following examples, which are not intended to be limiting.

Example 1

Illustrated in this example are various methods for producing the biofunctional coating compositions according to the present invention. Many of the peptides comprising the binding domains in the biofunctional coating composition according to the present invention (i.e., a surface-binding domain and an endothelial-binding domain) were developed using phage display technology.

A. Phage Screening and Selections.

Phage display technology is well-known in the art, and can be used to identify additional peptides for use as binding domains in the interfacial binding materials according to the present invention. In general, using phage display, a library of diverse peptides can be presented to a target substrate, and peptides that specifically bind to the substrate can be selected for use as binding domains. Multiple serial rounds of selection, called "panning," may be used. As is known in the art, any one of a variety of libraries and panning methods can be employed to identify a binding domain that is useful in a biofunctional coating composition according to the present invention. Panning methods can include, for example, solution phase screening, solid phase screening, or cell-based screening. Once a candidate binding domain is identified, directed or random mutagenesis of the sequence may be used to optimize the binding properties (including one or more of specificity and avidity) of the binding domain.

For example, a variety of different phage display libraries were screened for peptides that bind to a selected target substrate (e.g., a substrate selected to find a binding domain useful in the present invention). The substrate was either bound to or placed in (depending on the selected substrate) the wells of a 96 well microtiter plate. Nonspecific binding sites on the well surface of the polystyrene microtiter plate were blocked with a buffer containing 1% bovine serum albumin after overnight incubation at 4° C. The wells were then washed 5 times with a buffer containing phosphate buffered saline with Tween™ 20 ("PBS-T"). Each library was diluted in PBS-T and added at a concentration of $10^{10}$ pfu/ml in a total volume of 100 µl. After 3 hour of incubation at room temperature with shaking at 50 rpm, unbound phage were removed by multiple washes with PBS-T. Bound phage were recovered by denaturation with 0.1 M glycine buffer, pH2.2. The eluted phage were neutralized with phosphate buffer, and then added to *E. coli* cells in growth media. The cell and phage-containing media was cultured by incubation overnight at 37° C. in a shaker at 200 rpm. Phage-containing supernatant was harvested from the culture after centrifuging the culture. Second and third rounds of selection were performed in a similar manner to that of the first round of selection, using the amplified phage from the previous round as input. To detect phage that specifically bind to the selected substrate, enzyme-linked immunosorbent (ELISA-type) assays were performed using an anti-phage antibody conjugated to a detector molecule, followed by the detection and quantitation of the amount of detector molecule bound in the assay. The DNA sequences encoding peptides from the phage that specifically bind to the selected substrate were then determined; i.e., the sequence encoding the peptide is located as an insert in the phage genome, and can be sequenced to yield the corresponding amino acid sequence displayed on the phage surface.

As a specific illustrative example, titanium (in percent: Ti6Al4V) beads of approximately 5/32 of an inch diameter were washed with 70% ethanol, 40% nitric acid, distilled water, 70% ethanol, and acetone to remove any surface contaminants. One titanium bead was placed per well of 96-well polypropylene plate. Nonspecific binding sites on the titanium and the surface of the polypropylene were blocked with 1% bovine serum albumin (BSA) in PBS. The plate was incubated for 1 hour at room temperature with shaking at 50 rpm. The wells were then washed 5 times with 300 µl of PBS. Each library was diluted in PBS+1% BSA and was added at a concentration of $10^{10}$ pfu/ml in a total volume of 250 µl. After a 3 hour incubation at room temperature and shaking at 50 rpm, unbound phage were removed by washing 3 time with 300 µl of PBS-T. To recover the phage bound to the titanium beads, bound phage were released by treating with 50 mM glycine, pH 2 for 10 minutes followed by a 10 minute treatment with 100 mM ethanolamine, pH 12. The eluted phage were pooled, neutralized with 200 µl of 200 mM $NaPO_4$ pH 7. The eluted phage and the beads were added directly to *E. coli* DH5αF' cells in 2× YT media. The mixture was incubated overnight in a 37° C. shaker at 210 rpm. Phage supernatant was then harvested after spinning at 8500×g for 10 minutes. Second and third rounds of selection were performed in a similar manner to that of the first round, using the 50 µl of amplified phage from the previous round as input diluted with 200 µl of PBS+1% BSA. The fourth round of selection was carried out in a similar fashion; however, the washes were modified. After a 4 hour binding reaction, the beads were washed five times with PBS-T, the beads were moved to a clean polypropylene plate with 2 ml wells, 1 ml of PBS+1% BSA was added to each well and the washing was incubated overnight at room temperature with shaking at 50 rpm. The next morning the phage were eluted and amplified in the same manner described for rounds 1-3. Individual clonal phage were then isolated and tested by plating out dilutions of phage pools to obtain single plaques. To detect phage that specifically bound to titanium, conventional ELISAs were performed using an anti-M13 phage antibody conjugated to horseradish-peroxidase, followed by the addition of chromogenic agent ABTS (2,2'-azinobis(3-ethylbenzthiazoline-6-sulfonic acid). Relative binding strengths of the phage were determined by testing serial dilutions of the phage for binding to titanium in an ELISA. The DNA sequence encoding peptides that specifically bound titanium was determined. The sequence encoding the peptide insert was located in the phage genome and translated to yield the corresponding amino acid sequence displayed on the phage surface.

B. Binding Domain Characterizations and Synthesis

Relative binding strengths of the peptides were determined by testing serial dilutions of the peptide for binding to the selected substrate (as compared to a substrate used as a negative control; i.e. a substrate other than the selected substrate). Plotting the absorbance observed across the concentration range for each peptide sequence yielded a binding curve and rough dissociation constant ("$K_D$") of the peptides to its target substrate. The goal of the screenings and selections is to identify one or more peptides that bind to the selected substrate with binding specificity, preferably with an EC50 of less than or equal to about 10 µM, and more preferably, in the nanomolar range (<1 µM). Thus, in a preferred embodiment, in the methods and compositions according to the present invention, a preferred surface-binding domain comprises a peptide demonstrating binding specificity for the selected target (e.g., the material of the at least one surface of the medical device to be bound by the surface-binding domain) with an EC50 of less than or equal to about 10 µM, and more preferably, in the nanomolar range (<1 µM). Also in a preferred embodiment, in the methods and compositions according to the present invention, a preferred endothelial-binding domain comprises a peptide demonstrating binding specificity for the selected target (e.g., the cells of endothelial cell lineage to be bound by the endothelial-binding domain) with an EC50 of less than or equal to about 10 µM, and more preferably, in the nanomolar range (<1 µM).

As a specific example, titanium beads were blocked with 1% BSA in PBS for 30 minutes at room temperature. Stock solutions of each peptide being tested for binding affinity for titanium was prepared by dissolving 1-2 mg peptide in water. The final concentration of each peptide was determined using the optical density at 280 nm and the extinction coefficient for each peptide containing one or more of a tryptophan or tyrosine, and by a weight percent method for all other peptides. The peptides were prepared at 200 µM. A dilution series was then prepared for each peptide sample. Each peptide underwent a threefold dilution in 1% BSA in PBS. The peptides were incubated with the titanium beads for 1 hour at room temperature. Beads were then washed two times with PBS-T. Streptavidin-alkaline phosphatase was then added to the beads at a dilution of 1:500, and incubated for 30 minutes at room temperature. Beads were washed two times with PBS-T. PNPP (p-nitrophenyl phosphate) was used to develop the assay, and the absorbance was recorded at 405 nm. An estimate of the relative affinity (binding specificity, EC50) of a peptide for titanium can be made by determining the concentration of peptide that gives one-half the maximal signal in the assay.

As known to those skilled in the art and methods known in the art, peptides may be synthesized by any method for peptide synthesis including, but not limited to, solid phase synthesis, solution phase synthesis, and a combination thereof. For example, peptides comprising binding domains useful in the present invention were synthesized on a peptide synthesizer using standard solid-phase synthesis techniques, and using standard FMOC peptide chemistry. After all residues were coupled, simultaneous cleavage and side chain deprotection was performed using standard methods and reagents known in the art. After cleavage from the resin, the peptides were precipitated, and the precipitate was lyophilized. The peptides were then purified using reverse-phase high performance liquid chromatography; and peptide identity was confirmed with mass spectrometry.

In some instances, the peptides comprised modifications; i.e., were blocked at the N-terminus and/or at the C-terminus, and/or were linked to another peptide. Using these methods, for example, a surface-binding domain of a selected binding specificity (e.g., to a surface of a medical device) may be linked to an endothelial-binding domain (having binding specificity to cells of endothelial cell lineage), in forming a biofunctional coating composition according to the present invention. As apparent to one skilled in the art, a method of preference for linking a linker molecule to a binding domain will vary according to the reactive groups present on each molecule. Protocols for covalently linking two molecules using reactive groups are well known to one of skill in the art. As previously described herein, using methods well known to those skilled in the art, two binding domains may be coupled by a linker to form a biofunctional coating composition according to the present invention by synthesizing a single contiguous peptide comprising a first binding domain (e.g., a surface-binding domain), a linker comprising 3 or more amino acids (e.g., GSS), and a second binding domain (e.g., an endothelial-binding domain). The terms "first" and "second" are only used for purposes of ease of description, and is not intended to be construed as to limiting the order of the synthesis. In other words, the first binding domain may comprise an endothelial-binding domain, and the second binding domain may comprise the surface-binding domain. In an alternate method, at least one first binding domain having been avidinated (using streptavidin, avidin, or a functional derivative thereof, and methods known in the art) may be coupled to at least one second binding domain having been biotinylated (using biotin, and methods known in the art), in forming a biofunctional coating composition according to the present invention. In this example, the avidin-biotin molecules serve as the linker for coupling at least one surface-binding domain to at least one endothelial-binding domain in forming an interfacial biomaterial according to the present invention.

Example 2

This example illustrates peptides comprising surface-binding domains which may be used in the methods and biofunctional coating compositions according to the present invention. As described herein in more detail, a surface-binding domain comprises a peptide that specifically binds to the surface of a medical device, via the material of which the surface is comprised and for which the surface-binding domain has binding specificity. In that regard, a surface-binding domain may bind to any material which is used to make a medical device, and comprises a surface of the medical device, wherein the material may be selected from the group consisting of a metal, a metal oxide, a non-metal oxide, a ceramic, a polymer (such as, for example, a synthetic polymer such as a polyurethane, a rubber, a plastic, an acrylic, a silicone), and combinations thereof. Developed using the methods described in Example 1 herein, and as described in U.S. patent application Ser. No. 10/300,694 (published as US 20030185870), and U.S. patent application Ser. No. 11/152,974 (published as US 20060051395) (each licensed or assigned to the present applicant; the disclosures of which are herein incorporated by reference), exemplary peptides having binding specificity for a surface of a medical device include, but are not limited to the following.

Table 1 illustrates exemplary surface-binding domains, which may be used in the methods and for biofunctional coating compositions according to the present invention, having binding specificity for a polymer, and comprising: SEQ ID NOs:1-22 that specifically bind to polystyrene; SEQ ID NO:23 that specifically binds to polyurethane; SEQ ID NOs: 24-37 that specifically binds to polyglycolic acid; SEQ ID NOs: 38-43 that specifically bind to polycarbonate; SEQ ID NOs: 44-54 that specifically bind to nylon; and SEQ ID NOs: 55 and 56 that specifically bind to teflon.

TABLE 1

| SEQ ID NO: | Amino acid sequence (single letter code) |
|---|---|
| Binding specificity for polystyrene | |
| 1 | FLSFVFPASAWGG |
| 2 | FYMPFGPTWWQHV |
| 3 | LFSWFLPTDNYPV |
| 4 | FMDIWSPWHLLGT |
| 5 | FSSLFFPHWPAQL |
| 6 | SCAMAQWFCDRAEPHHVIS |
| 7 | SCNMSHLTGVSLCDSLATS |
| 8 | SCVYSFIDGSGCNSHSLGS |
| 9 | SCSGFHLLCESRSMQRELS |
| 10 | SCGILCSAFPFNNHQVGAS |
| 11 | SCCSMFFKNVSYVGASNPS |
| 12 | SCPIWKYCDDYSRSGSIFS |
| 13 | SCLFNSMKCLVLILCFVS |
| 14 | SCYVNGHNSVWVVVFWGVS |
| 15 | SCDFVCNVLFNVNHGSNMS |
| 16 | SCLNKFFVLMSVGLRSYTS |
| 17 | SCCNHNSTSVKDVQFPTLS |
| 18 | FFPSSWYSHLGVL |
| 19 | FFGFDVYDMSNAL |
| 20 | LSFSDFYFSEGSE |
| 21 | FSYSVSYAHPEGL |
| 22 | LPHLIQYRVLLVS |
| Binding specificity for polyurethane | |
| 23 | SCYVNGHNSVWWVFWGVS |
| Binding specificity of polyglycolic acid | |
| 24 | SCNSFMFINGSFKETGGCS |
| 25 | SCFGNLGNLIYTCDRLMPS |
| 26 | SCSFFMPWCNFLNGEMAVS |
| 27 | SCFGNVFCVYNQFAAGLFS |
| 28 | SCCFINSNFSVMNHSLFKS |
| 29 | SCDYFSFLECFSNGWSGAS |
| 30 | SCWMGLFECPDAWLHDWDS |
| 31 | SCFWYSWLCSASSSDALIS |
| 32 | SCFGNFLSFGFNCESALGS |
| 33 | SCLYCHLNNQFLSWVSGNS |
| 34 | SCFGFSDCLSWFVQPSTAS |
| 35 | SCNHLGFFSSFCDRLVENS |

TABLE 1-continued

| SEQ ID NO: | Amino acid sequence (single letter code) |
|---|---|
| 36 | SCGYFCSFYNYLDIGTASS |
| 37 | SCNSSSYSWYCWFGGSSPS |
| | Binding specificity for polycarbonate |
| 38 | FGHGWLNTLNLGW |
| 39 | FSPFSANLWYDMF |
| 40 | VFVPFGNWLSTSV |
| 41 | FWNVNYNPWGWNY |
| 42 | FYWDRLNVGWGLL |
| 43 | LYSTMYPGMSWLV |
| | Binding specificity for nylon |
| 44 | MASMTGGQYMGH |
| 45 | MASMTGGQWMGH |
| 46 | SCFYQNVISSSFAGNPWEC |
| 47 | SCNMLLNSLPLPSEDWSAC |
| 48 | SCPFTHSLALNTDRASPGC |
| 49 | SCFESDFPNVRHHVLKQSC |
| 50 | SCVFDSKHFSPTHSPHDVC |
| 51 | SCGDHMTDKNMPNSGISGC |
| 52 | SCDFFNRHGYNSGCEHSVC |
| 53 | SCGDHMTDKNMPNSGISGC |
| 54 | SCYYNGLWHHSNSGHKDC |
| | Binding specificity for Teflon |
| 55 | CWSRFRLFMLFCMFYLVS |
| 56 | CIKYPFLYCCLLSLFLFS |

Table 2 illustrates exemplary surface-binding domains, which may be used in the in the methods and for biofunctional coating compositions according to the present invention, having binding specificity for a metal (including a metal alloy), a metal oxide, or a non-metal oxide, and comprising: SEQ ID NOs:57-76 that specifically bind to titanium; and SEQ ID NOs: 77-94 that specifically bind to stainless steel.

TABLE 2

| SEQ ID NO: | Amino acid sequence (single letter code) |
|---|---|
| | Binding specificity for titanium |
| 57 | SCFWFLRWSLFIVLFTCCS |
| 58 | SCESVDCFADSRMAKVSMS |
| 59 | SCVGFFCITGSDVASVNSS |
| 60 | SCSDCLKSVDFIPSSLASS |
| 61 | SCAFDCPSSVARSPGEWSS |
| 62 | SCVDVMHADSPGPDGLNS |
| 63 | SCSSFEVSEMFTCAVSSYS |
| 64 | SCGLNFPLCSFVDFAQDAS |
| 65 | SCMLFSSVFDCGMLISDLS |
| 66 | SCVDYVMHADSPGPDGLNS |
| 67 | SCSENFMFNMYGTGVCTES |
| 68 | HKHPVTPRFFVVE |
| 69 | CNCYVTPNLLKHKCYKIC |
| 70 | CSHNHHKLTAKHQVAHKC |
| 71 | CDQNDIFYTSKKSHKSHC |
| 72 | SSDVYLVSHKHHLTRHNS |
| 73 | SDKCHKHWYCYESKYGGS |
| 74 | SDKSHKHWYSYESKYGGS |
| 75 | HHKLKHQMLHLNGG |
| 76 | GHHHKKDQLPQLGG |
| | Binding specificity for steel |
| 77 | CFVLNCHLVLDRP |
| 78 | SCFGNFLSFGFNCEYALGS |
| 79 | DGFFILYKNPDVL |
| 80 | NHQNQTN |
| 81 | ATHMVGS |
| 82 | GINPNFI |
| 83 | TAISGHF |
| 84 | LYGTPEYAVQPLR |
| 85 | CFLTQDYCVLAGK |
| 86 | VLHLDSYGPSVPL |
| 87 | WDSTGYLRPVST |
| 88 | VLQNATNVAPFVT |
| 89 | WWSSMPYVGDYTS |
| 90 | SSYFNLGLVKHNHVRHHDS |
| 91 | CHDHSNKYLKSWKHQQNC |
| 92 | SCKHDSEFIKKHVHAVKKC |
| 93 | SCHHLKHNTHKESKMHHEC |
| 94 | VNKMNRLWEPL |

While these exemplary peptide sequences are disclosed herein, one skilled in art will appreciate that the binding properties conferred by those sequences may be attributable to only some of the amino acids comprised by the sequences. Thus, a peptide which comprises only a portion of an exemplary amino acid sequence disclosed herein may have substantially the same binding properties as the exemplary peptide comprising the full-length amino acid sequence. Thus, also useful as surface-binding domains in the biofunctional coating compositions according to the present invention are peptides that comprise only 3, 4, 5, 6, 7, 8, 9, 10, 11, or 12 of the amino acids in a particular exemplary sequence provided herein. Such amino acids may be contiguous or non-contiguous so long as the desired property (e.g., substantially retaining binding specificity for the selected material) of the surface-binding domain is retained, as determined by an appropriate assay (described herein and/or as known to those skilled in the art). Such amino acids may be concentrated at the amino-terminal end of the exemplary peptide (for example, 4 amino acids may be concentrated in the first 4, 5, 6, 7, 8, 9, 10, 11, or 12 amino acids of the peptide), at the carboxy-terminal end of the exemplary peptide, or they may be dispersed throughout the exemplary peptide (e.g., acting as specific contact points, with the material for which the peptide has binding specificity, spaced apart from each other).

For example, consider surface-binding domains comprising amino acid sequences identified in Table 1 as SEQ ID NOs: 11, 18, and 19. A peptide comprising the amino acid sequence illustrated as SEQ ID NO:11, shares with SEQ ID NOs: 18 and 19 a consensus sequence of FFXXXXY (wherein X is any amino acid), except that in SEQ ID NO:11 the consensus sequence comprises amino acids internal to the amino acid sequence (e.g., between the N-terminal end and the C-terminal ends of the amino acid sequence of SEQ ID NO:11). It is also noted that in the phage display system used to identify surface-binding domains useful with the present invention, generally 2 amino acid residues (typically, serine) of phage sequence were displayed at the N-terminal end of the peptide sequence, and generally 2 amino acid residues (typically, serine and arginine) of phage sequence were displayed at the C-terminal end of the peptide sequence. While typically such phage amino acids adjoining the peptide displayed had no significant contribution to the binding specificity of the peptide, the surface-binding domains for use according to the present invention may also comprise, in their amino acid sequence, such phage amino acids adjoining the peptide at the N-terminus and at the C-terminus (e.g., SS and SR).

Example 3

This example illustrates peptides comprising endothelial-binding domains which may be used in the methods and biofunctional coating compositions according to the present invention. As described herein in more detail, an endothelial-binding domain comprises a peptide that specifically binds to cells of endothelial cell lineage via a cell-surface molecule or receptor or complex for which the endothelial-binding domain has binding specificity. Using the general methodology described in Example 1 herein, exemplary and preferred endothelial-binding domains have been developed.

In this illustrative example, cells of endothelial cell lineage used as target cells for the selection and screening process were human adipose-derived stem cells ("ADAS cells"). ADAS cells, CD34(−), VEGFR-2+ stem cells isolated from adipose tissue, have characteristics of endothelial progenitor cells, and can differentiate into endothelial cells upon the proper signals (e.g., exposure to VEGF). Fibroblasts (16 Lu fibroblast cell line) were used as non-target cells in the selection and screening process. Cells for pre-selections and selections were put into starvation conditions for 2-hours. Culture media was aspirated from each flask and 10-ml starvation media (minimal culture medium, with a buffer (balanced salt solution)+1% bovine serum albumin (BSA)) was added to each flask containing the cells. A polypropylene plate was also pre-blocked with buffer containing 1% BSA for 2-hours at room temperature. Fibroblasts were harvested by mechanical scraping, centrifuged, and resuspended in 400 µl buffer+1% BSA. 100 µL of this cell suspension was added to wells of pre-blocked polypropylene plates containing 200 µl buffer+1% BSA. To each well, 50 µL of pooled phage library was added and mixed thoroughly; and the cells and phage were incubated for 1 hour at 4° C. The polypropylene plate containing the cell and phage solution was centrifuged to pellet cells with attached phage. The supernatant containing unbound phage was removed and reserved.

The target cells, ADAS, were harvested by mechanical scraping, centrifuged, and resuspended in 400 µL buffer+1% BSA. ADAS cells (100 µl of this suspension) were added to each well of a pre-blocked polypropylene plate, along with supernatant containing unbound phage (from the fibroblast selection). The cells and phage were incubated for 1 hour at 4° C., and then centrifuged. The supernatant was aspirated, and the cells were washed again with 100 µL buffer+1% BSA. The final pellet of cells with attached phage was resuspended in 100 µl culture media, and the suspension was added to a culture tube containing culture media +100 µl E. coli DH5αf' cells. Phage were grown overnight at 37° C. with shaking in a 24 hour amplification period. Selection of phage using the ADAS cells was repeated twice more. Finally, individual phage plaques were picked and grown in culture medium and E. coli DH5αf' cells overnight at 37° C.

As an initial test for binding specificity, individual phage plaques were tested for binding to target (ADAS) cells and to non-target (16 Lu fibroblasts) cell lines. A phage clone showing binding specificity to ADAS cells, and low binding (similar to background) to non-target cells, was chosen for determining the amino acid sequence of the peptide displayed by the phage clone. Two peptides were synthesized from this clone, and comprise the amino acid sequences illustrated in SEQ ID NO:95 and SEQ ID NO:96 (also illustrated in Table 3). These peptides were tested in a variety of assay formats for binding specificity against a panel of cells and cell lines to compare binding to cells of endothelial cell lineage (e.g., human umbilical vein endothelial cells, human coronary artery endothelial cells, porcine coronary artery endothelial cells, and human endothelial progenitor cells) versus binding to cells of an origin other than endothelial cell lineage (e.g., human artery smooth muscle cells, porcine artery smooth muscle cells, platelets, and other mammalian cell lines). Binding to various cells of endothelial cell lineage was markedly greater (e.g., ranging from about 10 fold to about 100 fold) than to cells of an origin other than endothelial cell lineage; with preferred binding specificity for human umbilical vein endothelial cells and human coronary artery endothelial cells. Assays for characterizing binding specificity show that this preferred endothelial-binding domain has an EC50 of less than 10 µM, and more preferably less than 1 µM.

TABLE 3

| SEQ ID NO. | Amino Acid Sequence |
| --- | --- |
| 95 | SSSCQHVSLLRPSAALGPDNCCSRGSSGK |
| 96 | SSSCQHVSLLRPSAALGPDNCSRGSSGK |
| 97 | CQHVSLLRPSAALGPDNC |

During synthesis of the displayed peptides illustrated in Table 3, the N-terminal amino acids SSS and the C-terminal amino acids SR are phage sequence; and the amino acids GSSG represent an amino acid linker with amino acid K giving options for covalent attachment of another molecule (e.g., a surface-binding domain, or linker) via the epsilon amine. Thus, an endothelial-binding domain, comprising a peptide having an amino acid sequence illustrated in SEQ ID NO:97, comprises the amino acids primarily mediating the binding specificity for cells of endothelial cell lineage. In determining amino acids in key positions and their contributions for mediating binding specificity to cells of endothelial cell lineage (including, but not limited to, by making peptide variants and testing binding specificity and activity, demonstrating that two cysteines are required in the amino acid sequence to have binding activity and specificity), a preferred endothelial cell binding domain comprising a peptide variant or derivative of a peptide having the amino acid sequence of any one of SEQ ID NOs: 95, 96, and 97 comprises at least one peptide having a motif of SEQ ID NO:98, as follows.

SEQ ID NO:98 C—$Y_1$—X—X—X—$Y_2$—X—$Y_3$—P—X—X—X—$Y_2$—X—P—$Y_4$—$Y_1$—C; where

X is any amino acid;

$Y_1$ is Asn or Gln;

$Y_2$ is Leu or IIe;

$Y_3$ is a positively charged amino acid comprising Lys, Arg, or His; and $Y_4$ is a negatively charged amino acid comprising Glu or Asp.

Another way to express a preferred endothelial binding domain comprising a peptide comprising an amino acid sequence of SEQ ID NO:98, and in taking into consideration peptide variants or derivatives comprising amino acid deletions or additions thereof, and wherein such peptide has a length of at least 14 amino acids and no more than 20 amino acids is:

SEQ ID NO:98 C—$Y_1$—$(X)_n$—$Y_3$—P—(X) m-P—$Y_4$—Y—C; where

X is any amino acid, n is 1-6, m is 1-6; except that at least two Xs are $Y_2$ (each $Y_2$ is L or I, and both $Y_2$ may be the same (e.g., L, L; or I, I) or different (e.g., L, I; or I, L) amino acid) forming a heptad in the sequence, wherein the heptad begins with $Y_2$ and ends with $Y_2$ (e.g., $CY_1\underline{L}XXXY_3PX\underline{I}PY_4Y_1C$, $CY_1X\underline{I}Y_3PXXXX\underline{I}PY_4Y_1C$, $CY_1\underline{L}XY_3PXXXX\underline{L}PY_4Y_1C$, $CY_1\underline{L}XXY_3PXXX\underline{L}PY_4Y_1C$, $CY_1\underline{I}XXXY_3PX\underline{L}PY_4Y_1C$, $CY_1\underline{I}XXXY_3P\underline{I}PY_4Y_1C$, $CY_1X\underline{L}XXXY_3PX\underline{L}PY_4Y_1C$; (underlining for illustration of such heptad formed), and the like);

$Y_1$ is Asn or Gln;

$Y_3$ is a positively charged amino acid comprising Lys, Arg, or His; and $Y_4$ is a negatively charged amino acid comprising Glu or Asp.

Preferably, such peptide substantially retains binding specificity for a cell of endothelial cell lineage (binding to a cell of endothelial cell lineage with at least about 20% of the binding specificity as compared to a peptide comprising an amino acid sequence of any one of SEQ ID NO:95, 96, and 97), as can be determined by any method known in the art for determining binding specificity; for example, by quantitative flow cytometry (e.g., using Fluorescence-Activated Cell Sorting), quantitative cell-enzyme linked immunoassay (e.g., using methodology similar to that described in Example 1 herein), in vitro fluorescent cell staining with analysis by fluorescent microscopy, and the like; and using controls (e.g., no peptide, or a peptide known to lack binding specificity with the target cells) to assess background fluorescence.

Example 4

Peptides known and described in the art as having binding specificity or affinity (e.g., SEQ ID NO:99 has affinity for other cells as well) for endothelial cells include, but are not limited to, those illustrated in Table 4. Any one or more of these peptides may be used as an endothelial-binding domain in producing a biofunctional coating composition according to the present invention. It is noted that one or more of peptides having binding specificity for cells of endothelial cell lineage may bind to KDR and/or Flt-1 (also known as VEGFR-2), known receptors for binding of VEGF; and thus, have been described as having antiangiogenic activity. However, these peptides may still be useful as endothelial-binding domains, as each molecule of peptide of an endothelial binding domain may bind one molecule of a receptor for binding VEGF on a cell of endothelial cell lineage, leaving other molecules of that receptor available for binding VEGF and for promoting growth or proliferation of cells of endothelial cell lineage which are attached to at least one surface of a medical device via a biofunctional coating composition according to the present invention. Of the peptides described in the art as having binding specificity for endothelial cells, one or more such peptides may preferably be used as an endothelial-binding domain in accordance with the present invention to the exclusion of such peptides other than the one or more preferred peptides.

TABLE 4

| SEQ ID NO: | Amino Acid Sequence | Reference |
|---|---|---|
| 99 | RGDX | U.S. Pat. No. 5744515 |
| 100 | REDV | U.S. Pat. No. 5744515 |
| 101 | WQPPRARI | U.S. Pat. No. 5744515 |
| 102 | NGRX | U.S. Pat. No. 6974791 |
| 103 | CELRGDGWC | U.S. Pat. No. 6974791 |
| 104 | GCHSSTWRACG | US 2003/0166004 |
| 105 | GCPTPHSGTCG | US 2003/0166004 |
| 106 | GCMNQHSSACG | US 2003/0166004 |
| 107 | GCDSHKRLKCG | US 2003/0166004 |
| 108 | $(TKPPR)_n$, n = 1-10 | US 2006/0153775 |
| 109 | CPDLHHHMC | US 2006/0223756 |
| 110 | CLGQHAFTC | US 2006/0223756 |
| 111 | CSSNTAPHC | US 2006/0223756 |
| 112 | CHVLPNGNC | US 200610223756 |
| 113 | CKPQYPLSC | US 2006/0223756 |
| 114 | CQTARTPAC | US 2006/0223756 |
| 115 | CNQSQPKHC | US 2006/0223756 |
| 116 | CTPSKISVC | US 2006/0223756 |
| 117 | CVSPGPRLC | US 2006/0223756 |
| 118 | CYALSGVPC | US 2006/0223756 |
| 119 | CKHPPQPFC | US 2006/0223756 |

TABLE 4-continued

| SEQ ID NO: | Amino Acid Sequence | Reference |
|---|---|---|
| 120 | CHQSKPLLC | US 2006/0223756 |
| 121 | CPGPFSNWC | US 2006/0223756 |
| 122 | CPHKTHLPC | US 2006/0223756 |
| 123 | CVFPLSHYC | US 2006/0223756 |
| 124 | CNNIAPSSC | US 2006/0223756 |
| 125 | CTLGMQFQC | US 2006/0223756 |
| 126 | CTNPTGMLC | US 2006/0223756 |
| 127 | CSNMAPRSC | US 2006/0223756 |
| 128 | CSMAPNMSC | US 2006/0223756 |
| 129 | CSDLTMEAC | US 2006/0223756 |
| 130 | CPWPYKYSC | US 2006/0223756 |
| 131 | CFGGNFHRC | US 2006/0223756 |
| 132 | CLTTSQQTC | US 2006/0223756 |
| 133 | CTANSGSFC | US 2006/0223756 |
| 134 | CQEPLDESC | US 2006/0223756 |
| 135 | CQMSMFARC | US 2006/0223756 |
| 136 | CPLTPKAYC | US 2006/0223756 |
| 137 | CNNSHTALC | US 2006/0223756 |
| 138 | CLSSDITLC | US 2006/0223756 |
| 139 | CLTHGPKYC | US 2006/0223756 |
| 140 | CLGKDLRTC | US 2006/0223756 |
| 141 | CAPKTHPLC | US 2006/0223756 |
| 142 | CPTGLMKYC | US 2006/0223756 |
| 143 | CTWKAPLQC | US 2006/0223756 |
| 144 | CSHILGPSC | US 2006/0223756 |
| 145 | CLSTSQYSC | US 2006/0223756 |
| 146 | CGNSNPKSC | Cancer Biol Ther. 2004 Dec; 3 (12): 1232-5 |
| 147 | YCPRYVRRKLENELLVL | Acta Biochim. Biophys Sin (Shanghai), 2005 Apr; 37 (4):227-33. |
| 148 | NGYEIEWYSWVTHGMY | U.S. Pat. No. 6733755 |
| 149 | CNGYEIEWYSWVTHGMY | U.S. Pat. No. 6733755 |
| 150 | YLTMPTP | U.S. Pat. No. 6559126 |
| 151 | WPTPPYA | U.S. Pat. No. 6559126 |
| 152 | TPHNTVS | U.S. Pat. No. 6559126 |
| 153 | SLPAHAR | U.S. Pat. No. 6559126 |
| 154 | HSSLQTP | U.S. Pat. No. 6559126 |
| 155 | YSIPKSS | U.S. Pat. No. 6559126 |
| 156 | ALQPRYL | U.S. Pat. No. 6559126 |
| 157 | GREVD | U.S. Pat. No. 6140127 |

"X" is any amino acid

Example 5

In this example, illustrated are methods according to the present invention: (a) a method for manufacturing a medical device; (b) a method of coating a surface of a medical device so as to render the coated surface capable of adhering to cells of endothelial cell lineage; (c) a method for promoting endothelialization of at least one surface of a medical device; and (d) a method for promoting the adherence of cells of endothelial cell lineage to a medical device. The methods comprise contacting at least one surface of a medical device with an effective amount of a biofunctional coating composition under conditions suitable to produce a coating on the surface, wherein the biofunctional coating composition comprises at least one surface-binding domain and at least one endothelial-binding domain, and wherein the at least one surface-binding domain is coupled to the at least one endothelial-binding domain. Preferably, the at least one surface-binding domain is covalently coupled to the at least one endothelial-binding domain via a linker. The at least one surface-binding domain is the component of the biofunctional coating composition which is primarily responsible for binding the biofunctional coating composition to the one or more surfaces of the medical device to be coated.

With respect to these methods according to the present invention, and with respect to a biofunctional coating composition according to the present invention, and wherein at least one surface of the medical device to be coated comprises more than one material (e.g., two different metals; a metal and a metal oxide; a metal alloy and a polymer; two different polymers; and the like), the at least one surface-binding domain in the biofunctional coating may comprise a plurality (two or more) of types of surface-binding domains, wherein each type of surface-binding domain has binding specificity for a different surface material to be coated, as compared to the other surface-binding domains of which the biofunctional coating composition is comprised. Also with respect to this method according to the present invention, and with respect to a biofunctional coating composition according to the present invention, the at least one endothelial-binding domain may comprise more than one type (e.g., as determined by binding specificity of each type of endothelial-binding domain; for example, two or more different peptides, one peptide with binding specificity for endothelial cells, the other peptide with binding specificity for endothelial progenitor cells).

In these methods according to the present invention, when the biofunctional coating composition is contacted with the at least one surface of the medical device to be coated, either (a) the at least one endothelial-binding domain is bound to cells of endothelial cell lineage; or (b) the at least one endothelial-binding domain is not yet bound to cells of endothelial cell lineage. With respect to the latter, in a further step of coating, the coated surface of the medical device is then contacted with a sufficient amount of cells of endothelial cell lineage (in vitro or in vivo), for which the at least one endothelial-binding domain has binding specificity, under conditions suitable so that cells of endothelial cell lineage bind to the at least one endothelial-binding domain. In one example, the medical device may be contacted with cells of endothelial cell lineage (autologous or from a donor (e.g., allogeneic or xenogeneic) in vitro for the cells to bind and adhere to the coated surface of the device, and subsequently the device is implanted.

In another example, in a method according to the present invention for promoting endothelialization of a vascular device, generally one or more surfaces of the device to be exposed to vasculature once the device is implanted in an individual, is the one or mores surfaces of device desired and selected to be coated by a biofunctional coating composition according to the present invention. The method comprises the steps of: (a) contacting a biofunctional coating composition to at least one surface of a vascular device desired to be endothelialized, so that the biofunctional coating composition becomes bound to the at least one surface, in forming a coated surface on the device; wherein the biofunctional coating composition comprises at least one surface-binding domain coupled to at least one endothelial-cell binding domain; and (b) implanting the device into an individual in need of the device; wherein cells of endothelial cell lineage (produced by the individual, and circulating in the individual's vasculature) contact and attach to the coated surface of the device (via the biofunctional coating composition), wherein such contact and attachment promotes spread of cells of endothelial cell lineage over the coated surface of the device, in promoting endothelialization of the vascular device. Promoting endothelialization on the implanted device may further promote one or more of healing of tissue or vasculature adjacent to the implanted device, promote incorporation (integration) of the implanted device into the adjacent tissue, and reduce occurrence of thrombosis as related to the implanted device.

Conventional processes known in the art may be used to apply the biofunctional coating composition according to the present invention to the one or more surfaces of the medical device to be coated (in contacting the biofunctional coating composition with the one or more surfaces). Such processes are known to include, but are not limited to, dipping, brushing, spraying, vapor deposition, and electro-deposition. Formulations of the biofunctional coating composition according to the present invention may depend on the process used for coating the medical device. For example, a solution or suspension comprising the biofunctional coating composition may be applied through the spray nozzle of a spraying device, creating droplets that coat the surface of the medical device to be coated. The medical device is allowed to dry, and may then be further processed prior to use (e.g., washed in a solution (e.g., water or isotonic buffer) to remove excess biofunctional coating composition; by sterilization using any one or methods known in the art for sterilizing medical devices; etc.). Alternatively, the biofunctional coating composition and the medical device may all be sterilized prior to the process, and the process performed under sterile conditions.

In another process for applying the biofunctional coating to one or more surfaces of a medical device to be coated, the surface of the medical device to be coated is dipped into a liquid (e.g., solution or suspension, aqueous or solvent) containing the biofunctional coating composition in an amount effective to coat the surface. For example, the surface is dipped or immersed into a bath containing the biofunctional coating composition. Suitable conditions for applying the biofunctional coating composition include allowing the surface to be coated to remain in contact with the liquid containing the biofunctional coating composition for a suitable period of time (e.g., ranging from about 5 minutes to about 12 hours; more preferably, ranging from 15 minutes to 60 minutes), at a suitable temperature (e.g., ranging from 10° C. to about 50° C.; more preferably, ranging from room temperature to 37° C.). The coated medical device may then be further processed, as necessary for use (washing, sterilization, and the like).

In another process for applying the biofunctional coating to one or more surfaces of a medical device to be coated, the biofunctional coating composition according to the present invention is formulated in a dry powder (e.g., via air drying or lyophilizing the biofunctional coating composition). The powder comprising the biofunctional coating composition is then applied using methods known in the art for powder-coating the surface of the medical device to be coated. Typically, once applied, such powder coatings are then heat-treated (e.g., using infrared heating means) to complete the application process.

However, these illustrative processes for applying a biofunctional coating composition to a surface of a medical device are not exclusive, as other coating and stabilization methods may be employed (as one of skill in the art will be able to select the compositions and methods used to fit the needs of the particular device and purpose). For example, where the surface of the medical device to be coated is metallic in nature, a hydrophilic polymer (as previously described herein in more detail) may be used in conjunction (either applied simultaneously, or subsequently, to application of the biofunctional coating composition according to the present invention) so long as the biofunctional coating composition on the surface of the medical device substantially retains its function to bind to cells of endothelial cell origin in promoting one or more of adherence and endothelialization on the coated surface. In continuing this illustration, because of the elastomeric nature of the hydrophilic polymer, it may add to the stability of the biofunctional coating composition bound to the surface of the medical device should the device be subjected to mechanical forces or stress. Thus, the methods and compositions according to the present invention may also be used in conjunction with drug-eluting medical devices, or other coating technologies which provide one or more functional benefits to medical devices not provided by the biofunctional coating compositions according to the present invention.

Additionally, in a method according to the present invention, a coat comprising the biofunctional coating composition may be stabilized, for example, by air drying or by lyophilization. However, these treatments are not exclusive, and other coating and stabilization methods may be employed. Suitable coating and stabilization methods are known in the art. For example, the at least one surface of the vascular device to be coated with the biofunctional coating composition of the present invention may be pre-treated prior to the coating step so as to enhance one or more of the binding of the surface-binding domain to the material comprising the surface to be coated, and the consistency and uniformity of the coating. For example, such pretreatment may comprise etching or plasma treating the surface material of the device to be coated so as to make the surface more hydrophilic, in enhancing the binding of a surface binding domain comprising some hydrophobic amino acids in its amino acid sequence which interact with the hydrophilic moieties on the surface as part of binding specificity interactions.

In addition, or alternatively, in a further step, the at least one surface of the vascular device coated with the biofunctional coating composition of the present invention may treated, subsequent to coating but prior to implantation into an individual, so as to enhance endothelialization of the coated surface. For example, a matrix or layer of a biological substrate which supports endothelialization, and particularly growth (including proliferation) of endothelial cells adhering to the coated surface, may be added to (e.g., overlayed and/or adsorbed onto) the coated surface (for example, prior to or subsequent to binding and attachment to the coated surface by cells of endothelial cell lineage). Components of such layer or matrix can include a vascular biologic comprising one or more of collagen (e.g., type IV and/or type V), vitrogen, laminin, entactin, fibronectin, glycans (e.g., proteoglycans, glycosaminoglycans), and growth factors supporting endothelial cell growth (e.g., VEGF, EGF, FGF, heparin-binding epidermal-like growth factor, and the like).

Thus, in accordance with these methods of the present invention, a medical device may first be treated by a process which enhances binding (e.g., by increasing the hydrophilicity of, or the molecular adhesiveness of, the at least one surface of the device) of the biofunctional coating composition to the at least one treated surface of the device; contacting the biofunctional coating with the at least one treated surface in binding the biofunctional coating composition to the at least one treated surface in forming a coated surface. The method may further comprise contacting a vascular biologic with the coated surface in an amount effective to promote endothelialization on the coated surface. The methods may further comprise, prior to the implantation of the device, a step of contacting the coated device with cells of endothelial cell lineage in promoting one or more of attachment or adherence of the cells of the endothelial cell lineage, support for endothelial cell growth, and support for endothelial cell differentiation. For example, cells of the endothelial cell lineage may be purified and isolated using methods known in the art. For example, progenitor endothelial cells may be isolated from human peripheral blood using magnetic separation comprising magnetic beads coated with antibody to CD34. In another example, human umbilical vein endothelial cells may be isolated from umbilical cords by collagenase treatment of the blood vessel walls to release the endothelial cells, which may then be cultured in suitable supporting culture medium known in the art.

Example 6

It is apparent to one skilled in the art, that based on the amino acid sequence of the peptide comprising a preferred endothelial-binding domain and/or surface binding domain used in accordance with the present invention, that polynucleotides (nucleic acid molecules) encoding such a peptide (or variants thereof as described herein) may be synthesized or constructed, and that such a peptide may be produced by recombinant DNA technology as a means of manufacture (e.g., in culture) and/or in vivo production by introducing such polynucleotides in vivo. For example, it is apparent to one skilled in the art that more than one polynucleotide sequence can encode a peptide comprising SEQ ID NO:98 according to the present invention, and that such polynucleotides may be synthesized on the bases of triplet codons known to encode the amino acids of a peptide comprising the amino acid sequence of SEQ ID NO:98, third base degeneracy, and selection of triplet codon usage preferred by the host cell, typically a prokaryotic cell or eukaryotic cell (e.g., bacterial cells such as E. coli; yeast cells; mammalian cells; avian cells; amphibian cells; plant cells; fish cells; and insect cells; whether located in vitro or in vivo.) in which expression is desired. It would be routine for one skilled in the art to generate the degenerate variants described above, for instance, to optimize codon expression for a particular host (e.g., change codons in the bacteria mRNA to those preferred by a mammalian, plant or other bacterial host such as E. coli).

For purposes of illustration only, and not limitation, provided as SEQ ID NO:158 is a polynucleotide encoding an amino acid sequence of SEQ ID NO:98, from which, as apparent to one skilled in the art, codon usage will generally apply to polynucleotides encoding a preferred endothelial-binding domain comprising a peptide comprising the amino acid sequence illustrated in SEQ ID NO:98. Thus, for example, using SEQ ID NO: 158 in relation to SEQ ID NO:98, one skilled in the art could readily construct a polynucleotide encoding variants of the amino acid sequence illustrated in SEQ ID NO:98. In a preferred embodiment, a polynucleotide encoding a peptide comprising the amino acid sequence of SEQ ID NO:98 comprises a nucleic acid molecule encoding a peptide consisting of the amino acid sequence illustrated in SEQ ID NO:98, or an amino acid sequence having at least 95% identity (and more preferably, at least 90% identity) with SEQ ID NO:98, provided the encoded peptide substantially retains binding specificity for a cell of endothelial cell lineage.

In one illustrative embodiment, provided is a prokaryotic expression vector containing a polynucleotide encoding an endothelial cell binding domain for use in accordance with the present invention; and its use for the recombinant production of a peptide comprising the endothelial-binding domain. In one example, the polynucleotide may be positioned in a prokaryotic expression vector so that when the peptide is produced in bacterial host cells, it is produced as a fusion protein with other amino acid sequence (e.g., which assist in purification of the peptide; or as recombinantly coupled to a surface-binding domain). For example, there are sequences known to those skilled in the art which, as part of a fusion protein with a peptide desired to be expressed, facilitates production in inclusion bodies found in the cytoplasm of the prokaryotic cell used for expression and/or assists in purification of fusion proteins containing such sequence. Inclusion bodies may be separated from other prokaryotic cellular components by methods known in the art to include denaturing agents, and fractionation (e.g., centrifugation, column chromatography, and the like). In another example, there are commercially available vectors into which is inserted a desired nucleic acid sequence of interest to be expressed as a protein or peptide such that upon expression, the gene product also contains a plurality of terminal histidine residues ("His tags") that can be utilized in the purification of the gene product using methods standard in the art.

It is apparent to one skilled in the art that a nucleic acid sequence encoding an endothelial-binding domain comprising a peptide for use according to the present invention can be inserted into, and become part of a, nucleic acid molecule comprising a plasmid, or vectors other than plasmids; and other expression systems can be used including, but not limited to, bacteria transformed with a bacteriophage vector, or cosmid DNA; yeast containing yeast vectors; fungi containing fungal vectors; insect cell lines infected with virus (e.g. baculovirus); and mammalian cell lines having introduced therein (e.g., transfected or electroporated with) plasmid or viral expression vectors, or infected with recombinant virus (e.g. vaccinia virus, adenovirus, adeno-associated virus, retrovirus, etc.). Successful expression of the peptide requires that either the recombinant nucleic acid molecule comprising the encoding sequence of the peptide, or the vector itself, contain the necessary control elements for transcription and translation which is compatible with, and recognized by the particular host system used for expression.

Using methods known in the art of molecular biology, including methods described above, various promoters and enhancers can be incorporated into the vector or the recombinant nucleic acid molecule comprising the encoding sequence to increase the expression of the peptide, provided that the increased expression of the peptide is compatible with (for example, non-toxic to) the particular host cell system used. As apparent to one skilled in the art, the selection of the promoter will depend on the expression system used. Promoters vary in strength, i.e., ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, T7 promoter, recA promoter, ribosomal RNA promoter, the P.sub.R and P.sub.L promoters, lacUV5, ompF, bla, lpp, and the like, may be used to provide transcription of the inserted nucleotide sequence encoding the synthetic peptide. Commonly used mammalian promoters in expression vectors for mammalian expression systems are the promoters from mammalian viral genes. Examples include the SV40 early promoter, mouse mammary tumor virus LTR promoter, adenovirus major late promoter, herpes simplex virus promoter, and the CMV promoter.

In the case where expression of the peptide may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside ("IPTG"); trp operon is induced when tryptophan is absent in the growth media; and tetracycline can be use in mammalian expression vectors having a tet sensitive promoter). Thus, expression of the peptide may be controlled by culturing transformed or transfected cells under conditions such that the promoter controlling the expression from the encoding sequence is not induced, and when the cells reach a suitable density in the growth medium, the promoter can be induced for expression from the encoding sequence. Other control elements for efficient gene transcription or message translation are well known in the art to include enhancers, transcription or translation initiation signals, transcription termination and polyadenylation sequences, and the like.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept of the present invention; and thus, such modifications and/or adaptations are intended to be within the meaning and scope of the appended claims.

What is claimed is:

1. A method for coating a medical device, the method comprising contacting the medical device with a biofunctional coating composition to form a medical device having at least one coated surface; wherein the biofunctional coating composition comprises a surface-binding domain and an endothelial-cell binding domain; wherein the surface-binding domain comprises a peptide which binds to a material of which the medical device is comprised; wherein the endothelial-cell binding domain comprises a peptide comprising an amino acid sequence selected from the group consisting of SEQ ID NO: 95, SEQ ID NO: 96, SEQ ID NO: 97, SEQ ID NO: 98, and a combination thereof that binds to cells of endothelial cell lineage; and wherein the surface-binding domain and the endothelial-cell binding domain are coupled together.

2. The method according to claim 1, wherein the medical device comprises a vascular device.

3. The method according to claim 2, wherein the vascular device comprises a stent.

4. The method according to claim 1, wherein the at least one surface-binding domain and the at least one endothelial-cell binding domain are coupled via a linker.

5. The method according to claim 1, wherein the biofunctional coating composition comprises more than one type of surface-binding domain, and wherein each type of surface-binding domain is capable of binding to the surface material of the medical device.

6. The method according to claim 1, wherein the biofunctional coating composition comprises more than one type of endothelial-cell binding domain, and wherein each type of endothelial-binding domain has a binding specificity for cells of endothelial cell lineage that differs from another type of endothelial-binding domain present in the biofunctional coating composition.

7. A medical device comprising at least one surface of the medical device coated with a biofunctional coating composition, wherein the biofunctional coating composition comprises at least one surface-binding domain and at least one endothelial-cell binding domain; wherein a surface-binding domain comprises a peptide which binds to a material comprising a material selected from the group consisting of metal, metal oxide, non-metal oxide, ceramic, polymer, and a combination thereof; wherein an endothelial-cell binding domain comprises a peptide comprising an amino acid sequence selected from the group consisting of SEQ ID NO: 95, SEQ ID NO: 96, SEQ ID NO: 97, SEQ ID NO: 98, and a combination thereof that binds to cells of endothelial cell lineage; and wherein the at least one surface-binding domain and the at least one endothelial-cell binding domain are coupled together.

8. The medical device according to claim 7, wherein the medical device comprises a vascular device.

9. The medical device according to claim 8, wherein the vascular device comprises a stent.

10. The medical device according to claim 7, wherein the at least one surface-binding domain and the at least one endothelial-cell binding domain are coupled via a linker.

11. The medical device according to claim 7, wherein the biofunctional coating composition comprises more than one type of surface-binding domain, and wherein each type of surface-binding domain is capable of binding to the surface material of the medical device.

12. The medical device according to claim 7, wherein the biofunctional coating composition comprises more than one type of endothelial-binding domain, and wherein each type of endothelial-binding domain has a binding specificity for cells of endothelial cell lineage that differs from another type of endothelial-binding domain present in the biofunctional coating composition.

13. The medical device according to claim 7, further comprising cells of endothelial cell lineage.

14. A medical device comprising a biofunctional coating composition that promotes attachment of endothelial cells, wherein the biofunctional coating composition comprises a surface-binding domain coupled to an endothelial cell-binding domain, wherein the surface-binding domain comprises a peptide which binds to a material of which the medical device is comprised, and wherein an endothelial-cell binding domain comprises a peptide comprising an amino acid sequence selected from the group consisting of SEQ ID NO: 95, SEQ ID NO: 96, SEQ ID NO: 97, SEQ ID NO: 98, and a combination thereof that binds to cells of endothelial cell lineage.

15. The medical device according to claim 14, wherein the medical device comprises a vascular device.

16. The medical device according to claim 14, wherein the vascular device comprises a stent.

17. The medical device according to claim 14, wherein the surface-binding domain and the endothelial-binding domain are coupled via a linker.

18. The medical device according to claim 14, further comprising cells of endothelial cell lineage.

19. The medical device according to claim 14, wherein the biofunctional coating composition is multimeric.

20. The method according to claim 1, further comprising contacting the biofunctional coating composition with cells of endothelial cell lineage.

21. The method according to claim 1, wherein the material comprises a material selected from the group consisting of metal, metal oxide, non-metal oxide, ceramic, polymer, and a combination thereof.

22. The method according to claim 1, wherein the biofunctional coating composition is multimeric.

* * * * *

```
                        SEQUENCE LISTING

<160> NUMBER OF SEQ ID NOS: 158

<210> SEQ ID NO 1
<211> LENGTH: 13
<212> TYPE: PRT
<213> ORGANISM: Artificial
<220> FEATURE:
<223> OTHER INFORMATION: synthesized

<400> SEQUENCE: 1

Phe Leu Ser Phe Val Phe Pro Ala Ser Ala Trp Gly Gly
1               5                   10

<210> SEQ ID NO 2
<211> LENGTH: 13
<212> TYPE: PRT
<213> ORGANISM: Artificial
<220> FEATURE:
<223> OTHER INFORMATION: synthesized

<400> SEQUENCE: 2

Phe Tyr Met Pro Phe Gly Pro Thr Trp Trp Gln His Val
1               5                   10

<210> SEQ ID NO 3
<211> LENGTH: 13
<212> TYPE: PRT
<213> ORGANISM: Artificial
<220> FEATURE:
<223> OTHER INFORMATION: synthesized

<400> SEQUENCE: 3

Leu Phe Ser Trp Phe Leu Pro Thr Asp Asn Tyr Pro Val
1               5                   10
```

```
<210> SEQ ID NO 4
<211> LENGTH: 13
<212> TYPE: PRT
<213> ORGANISM: Artificial
<220> FEATURE:
<223> OTHER INFORMATION: synthesized

<400> SEQUENCE: 4

Phe Met Asp Ile Trp Ser Pro Trp His Leu Leu Gly Thr
1               5                   10

<210> SEQ ID NO 5
<211> LENGTH: 13
<212> TYPE: PRT
<213> ORGANISM: Artificial
<220> FEATURE:
<223> OTHER INFORMATION: synthesized

<400> SEQUENCE: 5

Phe Ser Ser Leu Phe Phe Pro His Trp Pro Ala Gln Leu
1               5                   10

<210> SEQ ID NO 6
<211> LENGTH: 19
<212> TYPE: PRT
<213> ORGANISM: Artificial
<220> FEATURE:
<223> OTHER INFORMATION: synthesized

<400> SEQUENCE: 6

Ser Cys Ala Met Ala Gln Trp Phe Cys Asp Arg Ala Glu Pro His His
1               5                   10                  15

Val Ile Ser

<210> SEQ ID NO 7
<211> LENGTH: 19
<212> TYPE: PRT
<213> ORGANISM: Artificial
<220> FEATURE:
<223> OTHER INFORMATION: synthesized

<400> SEQUENCE: 7

Ser Cys Asn Met Ser His Leu Thr Gly Val Ser Leu Cys Asp Ser Leu
1               5                   10                  15

Ala Thr Ser

<210> SEQ ID NO 8
<211> LENGTH: 19
<212> TYPE: PRT
<213> ORGANISM: Artificial
<220> FEATURE:
<223> OTHER INFORMATION: synthesized

<400> SEQUENCE: 8

Ser Cys Val Tyr Ser Phe Ile Asp Gly Ser Gly Cys Asn Ser His Ser
1               5                   10                  15

Leu Gly Ser

<210> SEQ ID NO 9
<211> LENGTH: 19
<212> TYPE: PRT
<213> ORGANISM: Artificial
<220> FEATURE:
<223> OTHER INFORMATION: synthesized
```

```
<400> SEQUENCE: 9

Ser Cys Ser Gly Phe His Leu Leu Cys Glu Ser Arg Ser Met Gln Arg
1               5                   10                  15

Glu Leu Ser

<210> SEQ ID NO 10
<211> LENGTH: 19
<212> TYPE: PRT
<213> ORGANISM: Artificial
<220> FEATURE:
<223> OTHER INFORMATION: synthesized

<400> SEQUENCE: 10

Ser Cys Gly Ile Leu Cys Ser Ala Phe Pro Phe Asn Asn His Gln Val
1               5                   10                  15

Gly Ala Ser

<210> SEQ ID NO 11
<211> LENGTH: 19
<212> TYPE: PRT
<213> ORGANISM: Artificial
<220> FEATURE:
<223> OTHER INFORMATION: synthesized

<400> SEQUENCE: 11

Ser Cys Cys Ser Met Phe Phe Lys Asn Val Ser Tyr Val Gly Ala Ser
1               5                   10                  15

Asn Pro Ser

<210> SEQ ID NO 12
<211> LENGTH: 19
<212> TYPE: PRT
<213> ORGANISM: Artificial
<220> FEATURE:
<223> OTHER INFORMATION: synthesized

<400> SEQUENCE: 12

Ser Cys Pro Ile Trp Lys Tyr Cys Asp Asp Tyr Ser Arg Ser Gly Ser
1               5                   10                  15

Ile Phe Ser

<210> SEQ ID NO 13
<211> LENGTH: 18
<212> TYPE: PRT
<213> ORGANISM: Artificial
<220> FEATURE:
<223> OTHER INFORMATION: synthesized

<400> SEQUENCE: 13

Ser Cys Leu Phe Asn Ser Met Lys Cys Leu Val Leu Ile Leu Cys Phe
1               5                   10                  15

Val Ser

<210> SEQ ID NO 14
<211> LENGTH: 19
<212> TYPE: PRT
<213> ORGANISM: Artificial
<220> FEATURE:
<223> OTHER INFORMATION: synthesized
```

```
<400> SEQUENCE: 14

Ser Cys Tyr Val Asn Gly His Asn Ser Val Trp Val Val Phe Trp
1               5                   10                  15

Gly Val Ser

<210> SEQ ID NO 15
<211> LENGTH: 19
<212> TYPE: PRT
<213> ORGANISM: Artificial
<220> FEATURE:
<223> OTHER INFORMATION: synthesized

<400> SEQUENCE: 15

Ser Cys Asp Phe Val Cys Asn Val Leu Phe Asn Val Asn His Gly Ser
1               5                   10                  15

Asn Met Ser

<210> SEQ ID NO 16
<211> LENGTH: 19
<212> TYPE: PRT
<213> ORGANISM: Artificial
<220> FEATURE:
<223> OTHER INFORMATION: synthesized

<400> SEQUENCE: 16

Ser Cys Leu Asn Lys Phe Phe Val Leu Met Ser Val Gly Leu Arg Ser
1               5                   10                  15

Tyr Thr Ser

<210> SEQ ID NO 17
<211> LENGTH: 19
<212> TYPE: PRT
<213> ORGANISM: Artificial
<220> FEATURE:
<223> OTHER INFORMATION: synthesized

<400> SEQUENCE: 17

Ser Cys Cys Asn His Asn Ser Thr Ser Val Lys Asp Val Gln Phe Pro
1               5                   10                  15

Thr Leu Ser

<210> SEQ ID NO 18
<211> LENGTH: 13
<212> TYPE: PRT
<213> ORGANISM: Artificial
<220> FEATURE:
<223> OTHER INFORMATION: synthesized

<400> SEQUENCE: 18

Phe Phe Pro Ser Ser Trp Tyr Ser His Leu Gly Val Leu
1               5                   10

<210> SEQ ID NO 19
<211> LENGTH: 13
<212> TYPE: PRT
<213> ORGANISM: Artificial
<220> FEATURE:
<223> OTHER INFORMATION: synthesized

<400> SEQUENCE: 19

Phe Phe Gly Phe Asp Val Tyr Asp Met Ser Asn Ala Leu
1               5                   10
```

```
<210> SEQ ID NO 20
<211> LENGTH: 13
<212> TYPE: PRT
<213> ORGANISM: Artificial
<220> FEATURE:
<223> OTHER INFORMATION: synthesized

<400> SEQUENCE: 20

Leu Ser Phe Ser Asp Phe Tyr Phe Ser Glu Gly Ser Glu
1               5                   10

<210> SEQ ID NO 21
<211> LENGTH: 13
<212> TYPE: PRT
<213> ORGANISM: Artificial
<220> FEATURE:
<223> OTHER INFORMATION: synthesized

<400> SEQUENCE: 21

Phe Ser Tyr Ser Val Ser Tyr Ala His Pro Glu Gly Leu
1               5                   10

<210> SEQ ID NO 22
<211> LENGTH: 13
<212> TYPE: PRT
<213> ORGANISM: Artificial
<220> FEATURE:
<223> OTHER INFORMATION: synthesized

<400> SEQUENCE: 22

Leu Pro His Leu Ile Gln Tyr Arg Val Leu Leu Val Ser
1               5                   10

<210> SEQ ID NO 23
<211> LENGTH: 19
<212> TYPE: PRT
<213> ORGANISM: Artificial
<220> FEATURE:
<223> OTHER INFORMATION: synthesized

<400> SEQUENCE: 23

Ser Cys Tyr Val Asn Gly His Asn Ser Val Trp Val Val Val Phe Trp
1               5                   10                  15

Gly Val Ser

<210> SEQ ID NO 24
<211> LENGTH: 19
<212> TYPE: PRT
<213> ORGANISM: Artificial
<220> FEATURE:
<223> OTHER INFORMATION: synthesized

<400> SEQUENCE: 24

Ser Cys Asn Ser Phe Met Phe Ile Asn Gly Ser Phe Lys Glu Thr Gly
1               5                   10                  15

Gly Cys Ser

<210> SEQ ID NO 25
<211> LENGTH: 19
<212> TYPE: PRT
<213> ORGANISM: Artificial
<220> FEATURE:
<223> OTHER INFORMATION: synthesized
```

```
<400> SEQUENCE: 25

Ser Cys Phe Gly Asn Leu Gly Asn Leu Ile Tyr Thr Cys Asp Arg Leu
1               5                   10                  15

Met Pro Ser

<210> SEQ ID NO 26
<211> LENGTH: 19
<212> TYPE: PRT
<213> ORGANISM: Artificial
<220> FEATURE:
<223> OTHER INFORMATION: synthesized

<400> SEQUENCE: 26

Ser Cys Ser Phe Phe Met Pro Trp Cys Asn Phe Leu Asn Gly Glu Met
1               5                   10                  15

Ala Val Ser

<210> SEQ ID NO 27
<211> LENGTH: 19
<212> TYPE: PRT
<213> ORGANISM: Artificial
<220> FEATURE:
<223> OTHER INFORMATION: synthesized

<400> SEQUENCE: 27

Ser Cys Phe Gly Asn Val Phe Cys Val Tyr Asn Gln Phe Ala Ala Gly
1               5                   10                  15

Leu Phe Ser

<210> SEQ ID NO 28
<211> LENGTH: 19
<212> TYPE: PRT
<213> ORGANISM: Artificial
<220> FEATURE:
<223> OTHER INFORMATION: synthesized

<400> SEQUENCE: 28

Ser Cys Cys Phe Ile Asn Ser Asn Phe Ser Val Met Asn His Ser Leu
1               5                   10                  15

Phe Lys Ser

<210> SEQ ID NO 29
<211> LENGTH: 19
<212> TYPE: PRT
<213> ORGANISM: Artificial
<220> FEATURE:
<223> OTHER INFORMATION: synthesized

<400> SEQUENCE: 29

Ser Cys Asp Tyr Phe Ser Phe Leu Glu Cys Phe Ser Asn Gly Trp Ser
1               5                   10                  15

Gly Ala Ser

<210> SEQ ID NO 30
<211> LENGTH: 19
<212> TYPE: PRT
<213> ORGANISM: Artificial
<220> FEATURE:
<223> OTHER INFORMATION: synthesized
```

```
<400> SEQUENCE: 30

Ser Cys Trp Met Gly Leu Phe Glu Cys Pro Asp Ala Trp Leu His Asp
1               5                   10                  15

Trp Asp Ser

<210> SEQ ID NO 31
<211> LENGTH: 19
<212> TYPE: PRT
<213> ORGANISM: Artificial
<220> FEATURE:
<223> OTHER INFORMATION: synthesized

<400> SEQUENCE: 31

Ser Cys Phe Trp Tyr Ser Trp Leu Cys Ser Ala Ser Ser Ser Asp Ala
1               5                   10                  15

Leu Ile Ser

<210> SEQ ID NO 32
<211> LENGTH: 19
<212> TYPE: PRT
<213> ORGANISM: Artificial
<220> FEATURE:
<223> OTHER INFORMATION: synthesized

<400> SEQUENCE: 32

Ser Cys Phe Gly Asn Phe Leu Ser Phe Gly Phe Asn Cys Glu Ser Ala
1               5                   10                  15

Leu Gly Ser

<210> SEQ ID NO 33
<211> LENGTH: 19
<212> TYPE: PRT
<213> ORGANISM: Artificial
<220> FEATURE:
<223> OTHER INFORMATION: synthesized

<400> SEQUENCE: 33

Ser Cys Leu Tyr Cys His Leu Asn Asn Gln Phe Leu Ser Trp Val Ser
1               5                   10                  15

Gly Asn Ser

<210> SEQ ID NO 34
<211> LENGTH: 19
<212> TYPE: PRT
<213> ORGANISM: Artificial
<220> FEATURE:
<223> OTHER INFORMATION: synthesized

<400> SEQUENCE: 34

Ser Cys Phe Gly Phe Ser Asp Cys Leu Ser Trp Phe Val Gln Pro Ser
1               5                   10                  15

Thr Ala Ser

<210> SEQ ID NO 35
<211> LENGTH: 19
<212> TYPE: PRT
<213> ORGANISM: Artificial
<220> FEATURE:
<223> OTHER INFORMATION: synthesized
```

```
<400> SEQUENCE: 35

Ser Cys Asn His Leu Gly Phe Phe Ser Ser Phe Cys Asp Arg Leu Val
1               5                   10                  15

Glu Asn Ser

<210> SEQ ID NO 36
<211> LENGTH: 19
<212> TYPE: PRT
<213> ORGANISM: Artificial
<220> FEATURE:
<223> OTHER INFORMATION: synthesized

<400> SEQUENCE: 36

Ser Cys Gly Tyr Phe Cys Ser Phe Tyr Asn Tyr Leu Asp Ile Gly Thr
1               5                   10                  15

Ala Ser Ser

<210> SEQ ID NO 37
<211> LENGTH: 19
<212> TYPE: PRT
<213> ORGANISM: Artificial
<220> FEATURE:
<223> OTHER INFORMATION: synthesized

<400> SEQUENCE: 37

Ser Cys Asn Ser Ser Ser Tyr Ser Trp Tyr Cys Trp Phe Gly Gly Ser
1               5                   10                  15

Ser Pro Ser

<210> SEQ ID NO 38
<211> LENGTH: 13
<212> TYPE: PRT
<213> ORGANISM: Artificial
<220> FEATURE:
<223> OTHER INFORMATION: synthesized

<400> SEQUENCE: 38

Phe Gly His Gly Trp Leu Asn Thr Leu Asn Leu Gly Trp
1               5                   10

<210> SEQ ID NO 39
<211> LENGTH: 13
<212> TYPE: PRT
<213> ORGANISM: Artificial
<220> FEATURE:
<223> OTHER INFORMATION: synthesized

<400> SEQUENCE: 39

Phe Ser Pro Phe Ser Ala Asn Leu Trp Tyr Asp Met Phe
1               5                   10

<210> SEQ ID NO 40
<211> LENGTH: 13
<212> TYPE: PRT
<213> ORGANISM: Artificial
<220> FEATURE:
<223> OTHER INFORMATION: synthesized

<400> SEQUENCE: 40

Val Phe Val Pro Phe Gly Asn Trp Leu Ser Thr Ser Val
1               5                   10
```

<210> SEQ ID NO 41
<211> LENGTH: 13
<212> TYPE: PRT
<213> ORGANISM: Artificial
<220> FEATURE:
<223> OTHER INFORMATION: synthesized

<400> SEQUENCE: 41

Phe Trp Asn Val Asn Tyr Asn Pro Trp Gly Trp Asn Tyr
1               5                   10

<210> SEQ ID NO 42
<211> LENGTH: 13
<212> TYPE: PRT
<213> ORGANISM: Artificial
<220> FEATURE:
<223> OTHER INFORMATION: synthesized

<400> SEQUENCE: 42

Phe Tyr Trp Asp Arg Leu Asn Val Gly Trp Gly Leu Leu
1               5                   10

<210> SEQ ID NO 43
<211> LENGTH: 13
<212> TYPE: PRT
<213> ORGANISM: Artificial
<220> FEATURE:
<223> OTHER INFORMATION: synthesized

<400> SEQUENCE: 43

Leu Tyr Ser Thr Met Tyr Pro Gly Met Ser Trp Leu Val
1               5                   10

<210> SEQ ID NO 44
<211> LENGTH: 12
<212> TYPE: PRT
<213> ORGANISM: Artificial
<220> FEATURE:
<223> OTHER INFORMATION: synthesized

<400> SEQUENCE: 44

Met Ala Ser Met Thr Gly Gly Gln Tyr Met Gly His
1               5                   10

<210> SEQ ID NO 45
<211> LENGTH: 12
<212> TYPE: PRT
<213> ORGANISM: Artificial
<220> FEATURE:
<223> OTHER INFORMATION: synthesized

<400> SEQUENCE: 45

Met Ala Ser Met Thr Gly Gly Gln Trp Met Gly His
1               5                   10

<210> SEQ ID NO 46
<211> LENGTH: 19
<212> TYPE: PRT
<213> ORGANISM: Artificial
<220> FEATURE:
<223> OTHER INFORMATION: synthesized

<400> SEQUENCE: 46

Ser Cys Phe Tyr Gln Asn Val Ile Ser Ser Ser Phe Ala Gly Asn Pro
1               5                   10                  15

Trp Glu Cys

```
<210> SEQ ID NO 47
<211> LENGTH: 19
<212> TYPE: PRT
<213> ORGANISM: Artificial
<220> FEATURE:
<223> OTHER INFORMATION: synthesized

<400> SEQUENCE: 47

Ser Cys Asn Met Leu Leu Asn Ser Leu Pro Leu Pro Ser Glu Asp Trp
1               5                   10                  15

Ser Ala Cys

<210> SEQ ID NO 48
<211> LENGTH: 19
<212> TYPE: PRT
<213> ORGANISM: Artificial
<220> FEATURE:
<223> OTHER INFORMATION: synthesized

<400> SEQUENCE: 48

Ser Cys Pro Phe Thr His Ser Leu Ala Leu Asn Thr Asp Arg Ala Ser
1               5                   10                  15

Pro Gly Cys

<210> SEQ ID NO 49
<211> LENGTH: 19
<212> TYPE: PRT
<213> ORGANISM: Artificial
<220> FEATURE:
<223> OTHER INFORMATION: synthesized

<400> SEQUENCE: 49

Ser Cys Phe Glu Ser Asp Phe Pro Asn Val Arg His His Val Leu Lys
1               5                   10                  15

Gln Ser Cys

<210> SEQ ID NO 50
<211> LENGTH: 19
<212> TYPE: PRT
<213> ORGANISM: Artificial
<220> FEATURE:
<223> OTHER INFORMATION: synthesized

<400> SEQUENCE: 50

Ser Cys Val Phe Asp Ser Lys His Phe Ser Pro Thr His Ser Pro His
1               5                   10                  15

Asp Val Cys

<210> SEQ ID NO 51
<211> LENGTH: 19
<212> TYPE: PRT
<213> ORGANISM: Artificial
<220> FEATURE:
<223> OTHER INFORMATION: synthesized

<400> SEQUENCE: 51

Ser Cys Gly Asp His Met Thr Asp Lys Asn Met Pro Asn Ser Gly Ile
1               5                   10                  15

Ser Gly Cys

<210> SEQ ID NO 52
<211> LENGTH: 19
<212> TYPE: PRT
<213> ORGANISM: Artificial
```

```
<220> FEATURE:
<223> OTHER INFORMATION: synthesized

<400> SEQUENCE: 52

Ser Cys Asp Phe Phe Asn Arg His Gly Tyr Asn Ser Gly Cys Glu His
1               5                   10                  15

Ser Val Cys

<210> SEQ ID NO 53
<211> LENGTH: 19
<212> TYPE: PRT
<213> ORGANISM: Artificial
<220> FEATURE:
<223> OTHER INFORMATION: synthesized

<400> SEQUENCE: 53

Ser Cys Gly Asp His Met Thr Asp Lys Asn Met Pro Asn Ser Gly Ile
1               5                   10                  15

Ser Gly Cys

<210> SEQ ID NO 54
<211> LENGTH: 19
<212> TYPE: PRT
<213> ORGANISM: Artificial
<220> FEATURE:
<223> OTHER INFORMATION: synthesized

<400> SEQUENCE: 54

Ser Cys Tyr Tyr Asn Gly Leu Val Val His His Ser Asn Ser Gly His
1               5                   10                  15

Lys Asp Cys

<210> SEQ ID NO 55
<211> LENGTH: 18
<212> TYPE: PRT
<213> ORGANISM: Artificial
<220> FEATURE:
<223> OTHER INFORMATION: synthesized

<400> SEQUENCE: 55

Cys Trp Ser Arg Phe Arg Leu Phe Met Leu Phe Cys Met Phe Tyr Leu
1               5                   10                  15

Val Ser

<210> SEQ ID NO 56
<211> LENGTH: 18
<212> TYPE: PRT
<213> ORGANISM: Artificial
<220> FEATURE:
<223> OTHER INFORMATION: synthesized

<400> SEQUENCE: 56

Cys Ile Lys Tyr Pro Phe Leu Tyr Cys Cys Leu Leu Ser Leu Phe Leu
1               5                   10                  15

Phe Ser

<210> SEQ ID NO 57
<211> LENGTH: 19
<212> TYPE: PRT
<213> ORGANISM: Artificial
<220> FEATURE:
<223> OTHER INFORMATION: synthesized
```

```
<400> SEQUENCE: 57

Ser Cys Phe Trp Phe Leu Arg Trp Ser Leu Phe Ile Val Leu Phe Thr
1               5                   10                  15

Cys Cys Ser

<210> SEQ ID NO 58
<211> LENGTH: 19
<212> TYPE: PRT
<213> ORGANISM: Artificial
<220> FEATURE:
<223> OTHER INFORMATION: synthesized

<400> SEQUENCE: 58

Ser Cys Glu Ser Val Asp Cys Phe Ala Asp Ser Arg Met Ala Lys Val
1               5                   10                  15

Ser Met Ser

<210> SEQ ID NO 59
<211> LENGTH: 19
<212> TYPE: PRT
<213> ORGANISM: Artificial
<220> FEATURE:
<223> OTHER INFORMATION: synthesized

<400> SEQUENCE: 59

Ser Cys Val Gly Phe Phe Cys Ile Thr Gly Ser Asp Val Ala Ser Val
1               5                   10                  15

Asn Ser Ser

<210> SEQ ID NO 60
<211> LENGTH: 19
<212> TYPE: PRT
<213> ORGANISM: Artificial
<220> FEATURE:
<223> OTHER INFORMATION: synthesized

<400> SEQUENCE: 60

Ser Cys Ser Asp Cys Leu Lys Ser Val Asp Phe Ile Pro Ser Ser Leu
1               5                   10                  15

Ala Ser Ser

<210> SEQ ID NO 61
<211> LENGTH: 19
<212> TYPE: PRT
<213> ORGANISM: Artificial
<220> FEATURE:
<223> OTHER INFORMATION: synthesized

<400> SEQUENCE: 61

Ser Cys Ala Phe Asp Cys Pro Ser Ser Val Ala Arg Ser Pro Gly Glu
1               5                   10                  15

Trp Ser Ser

<210> SEQ ID NO 62
<211> LENGTH: 18
<212> TYPE: PRT
<213> ORGANISM: Artificial
<220> FEATURE:
<223> OTHER INFORMATION: synthesized
```

-continued

```
<400> SEQUENCE: 62

Ser Cys Val Asp Val Met His Ala Asp Ser Pro Gly Pro Asp Gly Leu
1               5                   10                  15

Asn Ser

<210> SEQ ID NO 63
<211> LENGTH: 19
<212> TYPE: PRT
<213> ORGANISM: Artificial
<220> FEATURE:
<223> OTHER INFORMATION: synthesized

<400> SEQUENCE: 63

Ser Cys Ser Ser Phe Glu Val Ser Glu Met Phe Thr Cys Ala Val Ser
1               5                   10                  15

Ser Tyr Ser

<210> SEQ ID NO 64
<211> LENGTH: 19
<212> TYPE: PRT
<213> ORGANISM: Artificial
<220> FEATURE:
<223> OTHER INFORMATION: synthesized

<400> SEQUENCE: 64

Ser Cys Gly Leu Asn Phe Pro Leu Cys Ser Phe Val Asp Phe Ala Gln
1               5                   10                  15

Asp Ala Ser

<210> SEQ ID NO 65
<211> LENGTH: 19
<212> TYPE: PRT
<213> ORGANISM: Artificial
<220> FEATURE:
<223> OTHER INFORMATION: synthesized

<400> SEQUENCE: 65

Ser Cys Met Leu Phe Ser Ser Val Phe Asp Cys Gly Met Leu Ile Ser
1               5                   10                  15

Asp Leu Ser

<210> SEQ ID NO 66
<211> LENGTH: 19
<212> TYPE: PRT
<213> ORGANISM: Artificial
<220> FEATURE:
<223> OTHER INFORMATION: synthesized

<400> SEQUENCE: 66

Ser Cys Val Asp Tyr Val Met His Ala Asp Ser Pro Gly Pro Asp Gly
1               5                   10                  15

Leu Asn Ser

<210> SEQ ID NO 67
<211> LENGTH: 19
<212> TYPE: PRT
<213> ORGANISM: Artificial
<220> FEATURE:
<223> OTHER INFORMATION: synthesized
```

```
<400> SEQUENCE: 67

Ser Cys Ser Glu Asn Phe Met Phe Asn Met Tyr Gly Thr Gly Val Cys
1               5                   10                  15

Thr Glu Ser

<210> SEQ ID NO 68
<211> LENGTH: 13
<212> TYPE: PRT
<213> ORGANISM: Artificial
<220> FEATURE:
<223> OTHER INFORMATION: synthesized

<400> SEQUENCE: 68

His Lys His Pro Val Thr Pro Arg Phe Phe Val Val Glu
1               5                   10

<210> SEQ ID NO 69
<211> LENGTH: 18
<212> TYPE: PRT
<213> ORGANISM: Artificial
<220> FEATURE:
<223> OTHER INFORMATION: synthesized

<400> SEQUENCE: 69

Cys Asn Cys Tyr Val Thr Pro Asn Leu Leu Lys His Lys Cys Tyr Lys
1               5                   10                  15

Ile Cys

<210> SEQ ID NO 70
<211> LENGTH: 18
<212> TYPE: PRT
<213> ORGANISM: Artificial
<220> FEATURE:
<223> OTHER INFORMATION: synthesized

<400> SEQUENCE: 70

Cys Ser His Asn His His Lys Leu Thr Ala Lys His Gln Val Ala His
1               5                   10                  15

Lys Cys

<210> SEQ ID NO 71
<211> LENGTH: 18
<212> TYPE: PRT
<213> ORGANISM: Artificial
<220> FEATURE:
<223> OTHER INFORMATION: synthesized

<400> SEQUENCE: 71

Cys Asp Gln Asn Asp Ile Phe Tyr Thr Ser Lys Lys Ser His Lys Ser
1               5                   10                  15

His Cys

<210> SEQ ID NO 72
<211> LENGTH: 18
<212> TYPE: PRT
<213> ORGANISM: Artificial
<220> FEATURE:
<223> OTHER INFORMATION: synthesized

<400> SEQUENCE: 72

Ser Ser Asp Val Tyr Leu Val Ser His Lys His His Leu Thr Arg His
1               5                   10                  15

Asn Ser
```

<210> SEQ ID NO 73
<211> LENGTH: 18
<212> TYPE: PRT
<213> ORGANISM: Artificial
<220> FEATURE:
<223> OTHER INFORMATION: synthesized

<400> SEQUENCE: 73

Ser Asp Lys Cys His Lys His Trp Tyr Cys Tyr Glu Ser Lys Tyr Gly
1               5                   10                  15

Gly Ser

<210> SEQ ID NO 74
<211> LENGTH: 18
<212> TYPE: PRT
<213> ORGANISM: Artificial
<220> FEATURE:
<223> OTHER INFORMATION: synthesized

<400> SEQUENCE: 74

Ser Asp Lys Ser His Lys His Trp Tyr Ser Tyr Glu Ser Lys Tyr Gly
1               5                   10                  15

Gly Ser

<210> SEQ ID NO 75
<211> LENGTH: 14
<212> TYPE: PRT
<213> ORGANISM: Artificial
<220> FEATURE:
<223> OTHER INFORMATION: synthesized

<400> SEQUENCE: 75

His His Lys Leu Lys His Gln Met Leu His Leu Asn Gly Gly
1               5                   10

<210> SEQ ID NO 76
<211> LENGTH: 14
<212> TYPE: PRT
<213> ORGANISM: Artificial
<220> FEATURE:
<223> OTHER INFORMATION: synthesized

<400> SEQUENCE: 76

Gly His His His Lys Lys Asp Gln Leu Pro Gln Leu Gly Gly
1               5                   10

<210> SEQ ID NO 77
<211> LENGTH: 13
<212> TYPE: PRT
<213> ORGANISM: Artificial
<220> FEATURE:
<223> OTHER INFORMATION: synthesized

<400> SEQUENCE: 77

Cys Phe Val Leu Asn Cys His Leu Val Leu Asp Arg Pro
1               5                   10

<210> SEQ ID NO 78
<211> LENGTH: 19
<212> TYPE: PRT
<213> ORGANISM: Artificial
<220> FEATURE:
<223> OTHER INFORMATION: synthesized

```
<400> SEQUENCE: 78

Ser Cys Phe Gly Asn Phe Leu Ser Phe Gly Phe Asn Cys Glu Tyr Ala
1               5                   10                  15

Leu Gly Ser

<210> SEQ ID NO 79
<211> LENGTH: 13
<212> TYPE: PRT
<213> ORGANISM: Artificial
<220> FEATURE:
<223> OTHER INFORMATION: synthesized

<400> SEQUENCE: 79

Asp Gly Phe Phe Ile Leu Tyr Lys Asn Pro Asp Val Leu
1               5                   10

<210> SEQ ID NO 80
<211> LENGTH: 7
<212> TYPE: PRT
<213> ORGANISM: Artificial
<220> FEATURE:
<223> OTHER INFORMATION: synthesized

<400> SEQUENCE: 80

Asn His Gln Asn Gln Thr Asn
1               5

<210> SEQ ID NO 81
<211> LENGTH: 7
<212> TYPE: PRT
<213> ORGANISM: Artificial
<220> FEATURE:
<223> OTHER INFORMATION: synthesized

<400> SEQUENCE: 81

Ala Thr His Met Val Gly Ser
1               5

<210> SEQ ID NO 82
<211> LENGTH: 7
<212> TYPE: PRT
<213> ORGANISM: Artificial
<220> FEATURE:
<223> OTHER INFORMATION: synthesized

<400> SEQUENCE: 82

Gly Ile Asn Pro Asn Phe Ile
1               5

<210> SEQ ID NO 83
<211> LENGTH: 7
<212> TYPE: PRT
<213> ORGANISM: Artificial
<220> FEATURE:
<223> OTHER INFORMATION: synthesized

<400> SEQUENCE: 83

Thr Ala Ile Ser Gly His Phe
1               5

<210> SEQ ID NO 84
<211> LENGTH: 13
<212> TYPE: PRT
<213> ORGANISM: Artificial
<220> FEATURE:
<223> OTHER INFORMATION: synthesized
```

<400> SEQUENCE: 84

Leu Tyr Gly Thr Pro Glu Tyr Ala Val Gln Pro Leu Arg
1               5                   10

<210> SEQ ID NO 85
<211> LENGTH: 13
<212> TYPE: PRT
<213> ORGANISM: Artificial
<220> FEATURE:
<223> OTHER INFORMATION: synthesized

<400> SEQUENCE: 85

Cys Phe Leu Thr Gln Asp Tyr Cys Val Leu Ala Gly Lys
1               5                   10

<210> SEQ ID NO 86
<211> LENGTH: 13
<212> TYPE: PRT
<213> ORGANISM: Artificial
<220> FEATURE:
<223> OTHER INFORMATION: synthesized

<400> SEQUENCE: 86

Val Leu His Leu Asp Ser Tyr Gly Pro Ser Val Pro Leu
1               5                   10

<210> SEQ ID NO 87
<211> LENGTH: 13
<212> TYPE: PRT
<213> ORGANISM: Artificial
<220> FEATURE:
<223> OTHER INFORMATION: synthesized

<400> SEQUENCE: 87

Val Val Asp Ser Thr Gly Tyr Leu Arg Pro Val Ser Thr
1               5                   10

<210> SEQ ID NO 88
<211> LENGTH: 13
<212> TYPE: PRT
<213> ORGANISM: Artificial
<220> FEATURE:
<223> OTHER INFORMATION: synthesized

<400> SEQUENCE: 88

Val Leu Gln Asn Ala Thr Asn Val Ala Pro Phe Val Thr
1               5                   10

<210> SEQ ID NO 89
<211> LENGTH: 13
<212> TYPE: PRT
<213> ORGANISM: Artificial
<220> FEATURE:
<223> OTHER INFORMATION: synthesized

<400> SEQUENCE: 89

Trp Trp Ser Ser Met Pro Tyr Val Gly Asp Tyr Thr Ser
1               5                   10

<210> SEQ ID NO 90
<211> LENGTH: 19
<212> TYPE: PRT
<213> ORGANISM: Artificial
<220> FEATURE:
<223> OTHER INFORMATION: synthesized

```
<400> SEQUENCE: 90

Ser Ser Tyr Phe Asn Leu Gly Leu Val Lys His Asn His Val Arg His
1               5                   10                  15

His Asp Ser

<210> SEQ ID NO 91
<211> LENGTH: 18
<212> TYPE: PRT
<213> ORGANISM: Artificial
<220> FEATURE:
<223> OTHER INFORMATION: synthesized

<400> SEQUENCE: 91

Cys His Asp His Ser Asn Lys Tyr Leu Lys Ser Trp Lys His Gln Gln
1               5                   10                  15

Asn Cys

<210> SEQ ID NO 92
<211> LENGTH: 19
<212> TYPE: PRT
<213> ORGANISM: Artificial
<220> FEATURE:
<223> OTHER INFORMATION: synthesized

<400> SEQUENCE: 92

Ser Cys Lys His Asp Ser Glu Phe Ile Lys Lys His Val His Ala Val
1               5                   10                  15

Lys Lys Cys

<210> SEQ ID NO 93
<211> LENGTH: 19
<212> TYPE: PRT
<213> ORGANISM: Artificial
<220> FEATURE:
<223> OTHER INFORMATION: synthesized

<400> SEQUENCE: 93

Ser Cys His His Leu Lys His Asn Thr His Lys Glu Ser Lys Met His
1               5                   10                  15

His Glu Cys

<210> SEQ ID NO 94
<211> LENGTH: 11
<212> TYPE: PRT
<213> ORGANISM: Artificial
<220> FEATURE:
<223> OTHER INFORMATION: synthesized

<400> SEQUENCE: 94

Val Asn Lys Met Asn Arg Leu Trp Glu Pro Leu
1               5                   10

<210> SEQ ID NO 95
<211> LENGTH: 29
<212> TYPE: PRT
<213> ORGANISM: Artificial
<220> FEATURE:
<223> OTHER INFORMATION: synthesized
```

```
<400> SEQUENCE: 95

Ser Ser Ser Cys Gln His Val Ser Leu Leu Arg Pro Ser Ala Ala Leu
1               5                   10                  15

Gly Pro Asp Asn Cys Cys Ser Arg Gly Ser Ser Gly Lys
            20                  25

<210> SEQ ID NO 96
<211> LENGTH: 28
<212> TYPE: PRT
<213> ORGANISM: Artificial
<220> FEATURE:
<223> OTHER INFORMATION: synthesized

<400> SEQUENCE: 96

Ser Ser Ser Cys Gln His Val Ser Leu Leu Arg Pro Ser Ala Ala Leu
1               5                   10                  15

Gly Pro Asp Asn Cys Ser Arg Gly Ser Ser Gly Lys
            20                  25

<210> SEQ ID NO 97
<211> LENGTH: 18
<212> TYPE: PRT
<213> ORGANISM: Artificial
<220> FEATURE:
<223> OTHER INFORMATION: synthesized

<400> SEQUENCE: 97

Cys Gln His Val Ser Leu Leu Arg Pro Ser Ala Ala Leu Gly Pro Asp
1               5                   10                  15

Asn Cys

<210> SEQ ID NO 98
<211> LENGTH: 18
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (2)..(2)
<223> OTHER INFORMATION: X = Asn or Gln
<220> FEATURE:
<221> NAME/KEY: MISC_FEATURE
<222> LOCATION: (3)..(5)
<223> OTHER INFORMATION: X is any amino acid
<220> FEATURE:
<221> NAME/KEY: MISC_FEATURE
<222> LOCATION: (6)..(6)
<223> OTHER INFORMATION: X = Leu or Ile
<220> FEATURE:
<221> NAME/KEY: MISC_FEATURE
<222> LOCATION: (7)..(7)
<223> OTHER INFORMATION: X is any amino acid
<220> FEATURE:
<221> NAME/KEY: MISC_FEATURE
<222> LOCATION: (8)..(8)
<223> OTHER INFORMATION: X = a positively charged amino acid comprising
     Lys, Arg, or His
<220> FEATURE:
<221> NAME/KEY: MISC_FEATURE
<222> LOCATION: (10)..(12)
<223> OTHER INFORMATION: X is any amino acid
<220> FEATURE:
<221> NAME/KEY: MISC_FEATURE
<222> LOCATION: (13)..(13)
<223> OTHER INFORMATION: X = Leu or Ile
<220> FEATURE:
<221> NAME/KEY: MISC_FEATURE
<222> LOCATION: (14)..(14)
<223> OTHER INFORMATION: X is any amino acid
```

```
<220> FEATURE:
<221> NAME/KEY: MISC_FEATURE
<222> LOCATION: (16)..(16)
<223> OTHER INFORMATION: X is a negatively charged amino acid comprising
      Glu or Asp
<220> FEATURE:
<221> NAME/KEY: MISC_FEATURE
<222> LOCATION: (17)..(17)
<223> OTHER INFORMATION: X = Asn or Gln

<400> SEQUENCE: 98

Cys Xaa Xaa Xaa Xaa Xaa Xaa Xaa Pro Xaa Xaa Xaa Xaa Xaa Pro Xaa
1               5                   10                  15

Xaa Cys

<210> SEQ ID NO 99
<211> LENGTH: 4
<212> TYPE: PRT
<213> ORGANISM: Artificial
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 99

Arg Gly Asp Xaa
1

<210> SEQ ID NO 100
<211> LENGTH: 4
<212> TYPE: PRT
<213> ORGANISM: Artificial
<220> FEATURE:
<223> OTHER INFORMATION: synthesized

<400> SEQUENCE: 100

Arg Glu Asp Val
1

<210> SEQ ID NO 101
<211> LENGTH: 8
<212> TYPE: PRT
<213> ORGANISM: Artificial
<220> FEATURE:
<223> OTHER INFORMATION: synthesized

<400> SEQUENCE: 101

Trp Gln Pro Pro Arg Ala Arg Ile
1               5

<210> SEQ ID NO 102
<211> LENGTH: 4
<212> TYPE: PRT
<213> ORGANISM: Artificial
<220> FEATURE:
<223> OTHER INFORMATION: synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 102

Asn Gly Arg Xaa
1
```

```
<210> SEQ ID NO 103
<211> LENGTH: 9
<212> TYPE: PRT
<213> ORGANISM: Artificial
<220> FEATURE:
<223> OTHER INFORMATION: synthesized

<400> SEQUENCE: 103

Cys Glu Leu Arg Gly Asp Gly Trp Cys
1               5

<210> SEQ ID NO 104
<211> LENGTH: 11
<212> TYPE: PRT
<213> ORGANISM: Artificial
<220> FEATURE:
<223> OTHER INFORMATION: synthesized

<400> SEQUENCE: 104

Gly Cys His Ser Ser Thr Trp Arg Ala Cys Gly
1               5                   10

<210> SEQ ID NO 105
<211> LENGTH: 11
<212> TYPE: PRT
<213> ORGANISM: Artificial
<220> FEATURE:
<223> OTHER INFORMATION: synthesized

<400> SEQUENCE: 105

Gly Cys Pro Thr Pro His Ser Gly Thr Cys Gly
1               5                   10

<210> SEQ ID NO 106
<211> LENGTH: 11
<212> TYPE: PRT
<213> ORGANISM: Artificial
<220> FEATURE:
<223> OTHER INFORMATION: synthesized

<400> SEQUENCE: 106

Gly Cys Met Asn Gln His Ser Ser Ala Cys Gly
1               5                   10

<210> SEQ ID NO 107
<211> LENGTH: 11
<212> TYPE: PRT
<213> ORGANISM: Artificial
<220> FEATURE:
<223> OTHER INFORMATION: synthesized

<400> SEQUENCE: 107

Gly Cys Asp Ser His Lys Arg Leu Lys Cys Gly
1               5                   10

<210> SEQ ID NO 108
<211> LENGTH: 5
<212> TYPE: PRT
<213> ORGANISM: Artificial
<220> FEATURE:
<223> OTHER INFORMATION: synthesized

<400> SEQUENCE: 108

Thr Lys Pro Pro Arg
1               5
```

```
<210> SEQ ID NO 109
<211> LENGTH: 9
<212> TYPE: PRT
<213> ORGANISM: Artificial
<220> FEATURE:
<223> OTHER INFORMATION: synthesized

<400> SEQUENCE: 109

Cys Pro Asp Leu His His His Met Cys
1               5

<210> SEQ ID NO 110
<211> LENGTH: 9
<212> TYPE: PRT
<213> ORGANISM: Artificial
<220> FEATURE:
<223> OTHER INFORMATION: synthesized

<400> SEQUENCE: 110

Cys Leu Gly Gln His Ala Phe Thr Cys
1               5

<210> SEQ ID NO 111
<211> LENGTH: 9
<212> TYPE: PRT
<213> ORGANISM: Artificial
<220> FEATURE:
<223> OTHER INFORMATION: synthesized

<400> SEQUENCE: 111

Cys Ser Ser Asn Thr Ala Pro His Cys
1               5

<210> SEQ ID NO 112
<211> LENGTH: 9
<212> TYPE: PRT
<213> ORGANISM: Artificial
<220> FEATURE:
<223> OTHER INFORMATION: synthesized

<400> SEQUENCE: 112

Cys His Val Leu Pro Asn Gly Asn Cys
1               5

<210> SEQ ID NO 113
<211> LENGTH: 9
<212> TYPE: PRT
<213> ORGANISM: Artificial
<220> FEATURE:
<223> OTHER INFORMATION: synthesized

<400> SEQUENCE: 113

Cys Lys Pro Gln Tyr Pro Leu Ser Cys
1               5

<210> SEQ ID NO 114
<211> LENGTH: 9
<212> TYPE: PRT
<213> ORGANISM: Artificial
<220> FEATURE:
<223> OTHER INFORMATION: synthesized

<400> SEQUENCE: 114

Cys Gln Thr Ala Arg Thr Pro Ala Cys
1               5
```

```
<210> SEQ ID NO 115
<211> LENGTH: 9
<212> TYPE: PRT
<213> ORGANISM: Artificial
<220> FEATURE:
<223> OTHER INFORMATION: synthesized

<400> SEQUENCE: 115

Cys Asn Gln Ser Gln Pro Lys His Cys
1               5

<210> SEQ ID NO 116
<211> LENGTH: 9
<212> TYPE: PRT
<213> ORGANISM: Artificial
<220> FEATURE:
<223> OTHER INFORMATION: synthesized

<400> SEQUENCE: 116

Cys Thr Pro Ser Lys Ile Ser Val Cys
1               5

<210> SEQ ID NO 117
<211> LENGTH: 9
<212> TYPE: PRT
<213> ORGANISM: Artificial
<220> FEATURE:
<223> OTHER INFORMATION: synthesized

<400> SEQUENCE: 117

Cys Val Ser Pro Gly Pro Arg Leu Cys
1               5

<210> SEQ ID NO 118
<211> LENGTH: 9
<212> TYPE: PRT
<213> ORGANISM: Artificial
<220> FEATURE:
<223> OTHER INFORMATION: synthesized

<400> SEQUENCE: 118

Cys Tyr Ala Leu Ser Gly Val Pro Cys
1               5

<210> SEQ ID NO 119
<211> LENGTH: 9
<212> TYPE: PRT
<213> ORGANISM: Artificial
<220> FEATURE:
<223> OTHER INFORMATION: synthesized

<400> SEQUENCE: 119

Cys Lys His Pro Pro Gln Pro Phe Cys
1               5

<210> SEQ ID NO 120
<211> LENGTH: 9
<212> TYPE: PRT
<213> ORGANISM: Artificial
<220> FEATURE:
<223> OTHER INFORMATION: synthesized

<400> SEQUENCE: 120

Cys His Gln Ser Lys Pro Leu Leu Cys
1               5
```

```
<210> SEQ ID NO 121
<211> LENGTH: 9
<212> TYPE: PRT
<213> ORGANISM: Artificial
<220> FEATURE:
<223> OTHER INFORMATION: synthesized

<400> SEQUENCE: 121

Cys Pro Gly Pro Phe Ser Asn Trp Cys
1               5

<210> SEQ ID NO 122
<211> LENGTH: 9
<212> TYPE: PRT
<213> ORGANISM: Artificial
<220> FEATURE:
<223> OTHER INFORMATION: synthesized

<400> SEQUENCE: 122

Cys Pro His Lys Thr His Leu Pro Cys
1               5

<210> SEQ ID NO 123
<211> LENGTH: 9
<212> TYPE: PRT
<213> ORGANISM: Artificial
<220> FEATURE:
<223> OTHER INFORMATION: synthesized

<400> SEQUENCE: 123

Cys Val Phe Pro Leu Ser His Tyr Cys
1               5

<210> SEQ ID NO 124
<211> LENGTH: 9
<212> TYPE: PRT
<213> ORGANISM: Artificial
<220> FEATURE:
<223> OTHER INFORMATION: synthesized

<400> SEQUENCE: 124

Cys Asn Asn Ile Ala Pro Ser Ser Cys
1               5

<210> SEQ ID NO 125
<211> LENGTH: 9
<212> TYPE: PRT
<213> ORGANISM: Artificial
<220> FEATURE:
<223> OTHER INFORMATION: synthesized

<400> SEQUENCE: 125

Cys Thr Leu Gly Met Gln Phe Gln Cys
1               5

<210> SEQ ID NO 126
<211> LENGTH: 9
<212> TYPE: PRT
<213> ORGANISM: Artificial
<220> FEATURE:
<223> OTHER INFORMATION: synthesized

<400> SEQUENCE: 126

Cys Thr Asn Pro Thr Gly Met Leu Cys
1               5
```

```
<210> SEQ ID NO 127
<211> LENGTH: 9
<212> TYPE: PRT
<213> ORGANISM: Artificial
<220> FEATURE:
<223> OTHER INFORMATION: synthesized

<400> SEQUENCE: 127

Cys Ser Asn Met Ala Pro Arg Ser Cys
1               5

<210> SEQ ID NO 128
<211> LENGTH: 9
<212> TYPE: PRT
<213> ORGANISM: Artificial
<220> FEATURE:
<223> OTHER INFORMATION: synthesized

<400> SEQUENCE: 128

Cys Ser Met Ala Pro Asn Met Ser Cys
1               5

<210> SEQ ID NO 129
<211> LENGTH: 9
<212> TYPE: PRT
<213> ORGANISM: Artificial
<220> FEATURE:
<223> OTHER INFORMATION: synthesized

<400> SEQUENCE: 129

Cys Ser Asp Leu Thr Met Glu Ala Cys
1               5

<210> SEQ ID NO 130
<211> LENGTH: 9
<212> TYPE: PRT
<213> ORGANISM: Artificial
<220> FEATURE:
<223> OTHER INFORMATION: synthesized

<400> SEQUENCE: 130

Cys Pro Trp Pro Tyr Lys Tyr Ser Cys
1               5

<210> SEQ ID NO 131
<211> LENGTH: 9
<212> TYPE: PRT
<213> ORGANISM: Artificial
<220> FEATURE:
<223> OTHER INFORMATION: synthesized

<400> SEQUENCE: 131

Cys Phe Gly Gly Asn Phe His Arg Cys
1               5

<210> SEQ ID NO 132
<211> LENGTH: 9
<212> TYPE: PRT
<213> ORGANISM: Artificial
<220> FEATURE:
<223> OTHER INFORMATION: synthesized

<400> SEQUENCE: 132

Cys Leu Thr Thr Ser Gln Gln Thr Cys
1               5
```

<210> SEQ ID NO 133
<211> LENGTH: 9
<212> TYPE: PRT
<213> ORGANISM: Artificial
<220> FEATURE:
<223> OTHER INFORMATION: synthesized

<400> SEQUENCE: 133

Cys Thr Ala Asn Ser Gly Ser Phe Cys
1               5

<210> SEQ ID NO 134
<211> LENGTH: 9
<212> TYPE: PRT
<213> ORGANISM: Artificial
<220> FEATURE:
<223> OTHER INFORMATION: synthesized

<400> SEQUENCE: 134

Cys Gln Glu Pro Leu Asp Glu Ser Cys
1               5

<210> SEQ ID NO 135
<211> LENGTH: 9
<212> TYPE: PRT
<213> ORGANISM: Artificial
<220> FEATURE:
<223> OTHER INFORMATION: synthesized

<400> SEQUENCE: 135

Cys Gln Met Ser Met Phe Ala Arg Cys
1               5

<210> SEQ ID NO 136
<211> LENGTH: 9
<212> TYPE: PRT
<213> ORGANISM: Artificial
<220> FEATURE:
<223> OTHER INFORMATION: synthesized

<400> SEQUENCE: 136

Cys Pro Leu Thr Pro Lys Ala Tyr Cys
1               5

<210> SEQ ID NO 137
<211> LENGTH: 9
<212> TYPE: PRT
<213> ORGANISM: Artificial
<220> FEATURE:
<223> OTHER INFORMATION: synthesized

<400> SEQUENCE: 137

Cys Asn Asn Ser His Thr Ala Leu Cys
1               5

<210> SEQ ID NO 138
<211> LENGTH: 9
<212> TYPE: PRT
<213> ORGANISM: Artificial
<220> FEATURE:
<223> OTHER INFORMATION: synthesized

<400> SEQUENCE: 138

Cys Leu Ser Ser Asp Ile Thr Leu Cys
1               5

```
<210> SEQ ID NO 139
<211> LENGTH: 9
<212> TYPE: PRT
<213> ORGANISM: Artificial
<220> FEATURE:
<223> OTHER INFORMATION: synthesized

<400> SEQUENCE: 139

Cys Leu Thr His Gly Pro Lys Tyr Cys
1               5

<210> SEQ ID NO 140
<211> LENGTH: 9
<212> TYPE: PRT
<213> ORGANISM: Artificial
<220> FEATURE:
<223> OTHER INFORMATION: synthesized

<400> SEQUENCE: 140

Cys Leu Gly Lys Asp Leu Arg Thr Cys
1               5

<210> SEQ ID NO 141
<211> LENGTH: 9
<212> TYPE: PRT
<213> ORGANISM: Artificial
<220> FEATURE:
<223> OTHER INFORMATION: synthesized

<400> SEQUENCE: 141

Cys Ala Pro Lys Thr His Pro Leu Cys
1               5

<210> SEQ ID NO 142
<211> LENGTH: 9
<212> TYPE: PRT
<213> ORGANISM: Artificial
<220> FEATURE:
<223> OTHER INFORMATION: synthesized

<400> SEQUENCE: 142

Cys Pro Thr Gly Leu Met Lys Tyr Cys
1               5

<210> SEQ ID NO 143
<211> LENGTH: 9
<212> TYPE: PRT
<213> ORGANISM: Artificial
<220> FEATURE:
<223> OTHER INFORMATION: synthesized

<400> SEQUENCE: 143

Cys Thr Trp Lys Ala Pro Leu Gln Cys
1               5

<210> SEQ ID NO 144
<211> LENGTH: 9
<212> TYPE: PRT
<213> ORGANISM: Artificial
<220> FEATURE:
<223> OTHER INFORMATION: synthesized

<400> SEQUENCE: 144

Cys Ser His Ile Leu Gly Pro Ser Cys
1               5
```

<210> SEQ ID NO 145
<211> LENGTH: 9
<212> TYPE: PRT
<213> ORGANISM: Artificial
<220> FEATURE:
<223> OTHER INFORMATION: synthesized

<400> SEQUENCE: 145

Cys Leu Ser Thr Ser Gln Tyr Ser Cys
1               5

<210> SEQ ID NO 146
<211> LENGTH: 9
<212> TYPE: PRT
<213> ORGANISM: Artificial
<220> FEATURE:
<223> OTHER INFORMATION: synthesized

<400> SEQUENCE: 146

Cys Gly Asn Ser Asn Pro Lys Ser Cys
1               5

<210> SEQ ID NO 147
<211> LENGTH: 17
<212> TYPE: PRT
<213> ORGANISM: Artificial
<220> FEATURE:
<223> OTHER INFORMATION: synthesized

<400> SEQUENCE: 147

Tyr Cys Pro Arg Tyr Val Arg Arg Lys Leu Glu Asn Glu Leu Leu Val
1               5                   10                  15

Leu

<210> SEQ ID NO 148
<211> LENGTH: 16
<212> TYPE: PRT
<213> ORGANISM: Artificial
<220> FEATURE:
<223> OTHER INFORMATION: synthesized

<400> SEQUENCE: 148

Asn Gly Tyr Glu Ile Glu Trp Tyr Ser Trp Val Thr His Gly Met Tyr
1               5                   10                  15

<210> SEQ ID NO 149
<211> LENGTH: 17
<212> TYPE: PRT
<213> ORGANISM: Artificial
<220> FEATURE:
<223> OTHER INFORMATION: synthesized

<400> SEQUENCE: 149

Cys Asn Gly Tyr Glu Ile Glu Trp Tyr Ser Trp Val Thr His Gly Met
1               5                   10                  15

Tyr

<210> SEQ ID NO 150
<211> LENGTH: 7
<212> TYPE: PRT
<213> ORGANISM: Artificial
<220> FEATURE:
<223> OTHER INFORMATION: synthesized

```
<400> SEQUENCE: 150

Tyr Leu Thr Met Pro Thr Pro
1               5

<210> SEQ ID NO 151
<211> LENGTH: 7
<212> TYPE: PRT
<213> ORGANISM: Artificial
<220> FEATURE:
<223> OTHER INFORMATION: synthesized

<400> SEQUENCE: 151

Trp Pro Thr Pro Pro Tyr Ala
1               5

<210> SEQ ID NO 152
<211> LENGTH: 7
<212> TYPE: PRT
<213> ORGANISM: Artificial
<220> FEATURE:
<223> OTHER INFORMATION: synthesized

<400> SEQUENCE: 152

Thr Pro His Asn Thr Val Ser
1               5

<210> SEQ ID NO 153
<211> LENGTH: 7
<212> TYPE: PRT
<213> ORGANISM: Artificial
<220> FEATURE:
<223> OTHER INFORMATION: synthesized

<400> SEQUENCE: 153

Ser Leu Pro Ala His Ala Arg
1               5

<210> SEQ ID NO 154
<211> LENGTH: 7
<212> TYPE: PRT
<213> ORGANISM: Artificial
<220> FEATURE:
<223> OTHER INFORMATION: synthesized

<400> SEQUENCE: 154

His Ser Ser Leu Gln Thr Pro
1               5

<210> SEQ ID NO 155
<211> LENGTH: 7
<212> TYPE: PRT
<213> ORGANISM: Artificial
<220> FEATURE:
<223> OTHER INFORMATION: synthesized

<400> SEQUENCE: 155

Tyr Ser Ile Pro Lys Ser Ser
1               5

<210> SEQ ID NO 156
<211> LENGTH: 7
<212> TYPE: PRT
<213> ORGANISM: Artificial
<220> FEATURE:
<223> OTHER INFORMATION: synthesized
```

-continued

```
<400> SEQUENCE: 156

Ala Leu Gln Pro Arg Tyr Leu
1               5

<210> SEQ ID NO 157
<211> LENGTH: 5
<212> TYPE: PRT
<213> ORGANISM: Artificial
<220> FEATURE:
<223> OTHER INFORMATION: synthesized

<400> SEQUENCE: 157

Gly Arg Glu Val Asp
1               5

<210> SEQ ID NO 158
<211> LENGTH: 54
<212> TYPE: DNA
<213> ORGANISM: Artificial
<220> FEATURE:
<223> OTHER INFORMATION: synthesized

<400> SEQUENCE: 158
tgccaacacg ttagcttatt aagaccgtcc gctgctttag ggccggataa ttgc       54
```